(12) United States Patent
Kaula et al.

(10) Patent No.: US 10,668,276 B2
(45) Date of Patent: Jun. 2, 2020

(54) METHOD AND SYSTEM OF BRACKETING STIMULATION PARAMETERS ON CLINICIAN PROGRAMMERS

(71) Applicant: Greatbatch Ltd., Clarence, NY (US)

(72) Inventors: Norbert Kaula, Arvada, CO (US); Yohannes Iyassu, Denver, CO (US)

(73) Assignee: Cirtec Medical Corp., Brooklyn Park, MN (US)

( * ) Notice: Subject to any disclaimer, the term of this patent is extended or adjusted under 35 U.S.C. 154(b) by 1821 days.

(21) Appl. No.: 13/973,292

(22) Filed: Aug. 22, 2013

(65) Prior Publication Data

US 2014/0067016 A1    Mar. 6, 2014

Related U.S. Application Data

(60) Provisional application No. 61/695,700, filed on Aug. 31, 2012, provisional application No. 61/824,296, filed on May 16, 2013.

(51) Int. Cl.
*A61N 1/08* (2006.01)
*A61N 1/372* (2006.01)
(Continued)

(52) U.S. Cl.
CPC ........... *A61N 1/08* (2013.01); *A61N 1/37247* (2013.01); *G16H 40/63* (2018.01); *G16H 50/50* (2018.01); *A61N 1/36132* (2013.01)

(58) Field of Classification Search
CPC .. A61N 1/08; A61N 1/37247; A61N 1/36132; G16H 50/50; G16H 40/63
(Continued)

(56) References Cited

U.S. PATENT DOCUMENTS

| 4,432,360 A | 2/1984 | Mumford et al. |
| 5,286,202 A | 2/1994 | De Gyarfas et al. |

(Continued)

FOREIGN PATENT DOCUMENTS

| EP | 1192972 | 4/2002 |
| EP | 2277586 | 1/2011 |

(Continued)

OTHER PUBLICATIONS

Synalink Features, SynaMed Web Page, http://synamed.com/synalinkFeatures.html., Copyright 2010, 2 pgs.
(Continued)

*Primary Examiner* — Amanda K Hulbert
(74) *Attorney, Agent, or Firm* — Haynes and Boone, LLP; J Lowes; Eric Li

(57) ABSTRACT

The present disclosure involves a method of setting stimulation parameters for neurostimulation. A plurality of stimulation parameters available for bracketing is displayed. The stimulation parameters are selected from the group consisting of: stimulation current amplitude, pulse width, frequency, and contact location. Thereafter, in response to an input from a user, at least a subset of the stimulation parameters is selected for bracketing. A respective initial value is then obtained for each of the stimulation parameters in the selected subset. Thereafter, a bracketing process is used to generate a plurality of bracketed values for each of the stimulation parameters in the selected subset. The bracketed values are generated as a function of the initial value. A plurality of stimulation pulses is then delivered to a patient through a neurostimulator that is automatically programmed with a different combination of the bracketed values for the stimulation parameters for each stimulation pulse.

38 Claims, 15 Drawing Sheets

(51) Int. Cl.
*G16H 40/63* (2018.01)
*G16H 50/50* (2018.01)
*A61N 1/36* (2006.01)

(58) Field of Classification Search
USPC .................................................. 607/59, 30
See application file for complete search history.

(56) References Cited

U.S. PATENT DOCUMENTS

| | | | |
|---|---|---|---|
| 5,304,206 A | 4/1994 | Baker, Jr. et al. | |
| 5,312,446 A | 5/1994 | Holschbach et al. | |
| 5,370,672 A | 12/1994 | Fowler et al. | |
| 5,383,914 A | 1/1995 | O'Phelan | |
| 5,421,830 A | 6/1995 | Epstein et al. | |
| 5,628,776 A | 5/1997 | Paul et al. | |
| 5,713,937 A | 2/1998 | Nappholz et al. | |
| 5,722,999 A | 3/1998 | Snell | |
| 5,724,996 A | 3/1998 | Piunti | |
| 5,819,740 A | 10/1998 | Muhlenberg | |
| 5,879,374 A | 3/1999 | Powers et al. | |
| 5,905,500 A | 5/1999 | Kamen et al. | |
| 5,938,690 A | 8/1999 | Law et al. | |
| 6,016,447 A | 1/2000 | Juran et al. | |
| 6,016,448 A | 1/2000 | Busacker et al. | |
| 6,052,624 A | 4/2000 | Mann | |
| 6,083,156 A | 7/2000 | Lisiecki | |
| 6,148,233 A | 11/2000 | Owen et al. | |
| 6,154,675 A | 11/2000 | Juran et al. | |
| 6,216,036 B1 | 4/2001 | Jenkins et al. | |
| 6,246,414 B1 | 6/2001 | Kawasaki | |
| 6,249,705 B1 | 6/2001 | Snell | |
| 6,278,890 B1 | 8/2001 | Chassaing et al. | |
| 6,307,554 B1 | 10/2001 | Arai et al. | |
| 6,308,102 B1 | 10/2001 | Sieracki et al. | |
| 6,345,200 B1 | 2/2002 | Mouchawar et al. | |
| 6,386,882 B1 | 5/2002 | Linberg | |
| 6,442,432 B2 | 8/2002 | Lee | |
| 6,525,727 B1 | 2/2003 | Junkins et al. | |
| 6,564,104 B2 | 5/2003 | Nelson et al. | |
| 6,587,104 B1 | 7/2003 | Hoppe | |
| 6,611,267 B2 | 8/2003 | Migdal et al. | |
| 6,622,048 B1 | 9/2003 | Mann et al. | |
| 6,669,631 B2 | 12/2003 | Norris et al. | |
| 6,786,405 B2 | 9/2004 | Weidenhoefer | |
| 6,852,080 B2 | 2/2005 | Bardy | |
| 6,882,982 B2 | 4/2005 | McMenimen et al. | |
| 6,895,280 B2 | 5/2005 | Meadows et al. | |
| 6,920,360 B2 | 7/2005 | Lee et al. | |
| 6,931,155 B1 | 8/2005 | Gioia | |
| 6,961,448 B2 | 11/2005 | Nichols et al. | |
| 6,961,617 B1 | 11/2005 | Snell | |
| 7,003,349 B1 | 2/2006 | Andersson et al. | |
| 7,034,823 B2 | 4/2006 | Dunnet | |
| 7,058,453 B2 | 6/2006 | Nelson et al. | |
| 7,060,030 B2 | 6/2006 | Von Arx et al. | |
| 7,065,409 B2 | 6/2006 | Mazar | |
| 7,066,910 B2 | 6/2006 | Bauhahn et al. | |
| 7,076,303 B2 | 7/2006 | Linberg | |
| 7,087,015 B1 | 8/2006 | Comrie et al. | |
| 7,092,761 B1 | 8/2006 | Cappa et al. | |
| 7,107,102 B2 | 9/2006 | Daignault et al. | |
| 7,142,923 B2 | 11/2006 | North et al. | |
| 7,181,286 B2 | 2/2007 | Sieracki et al. | |
| 7,181,505 B2 | 2/2007 | Haller et al. | |
| 7,184,837 B2 | 2/2007 | Goetz | |
| 7,239,926 B2 | 7/2007 | Goetz | |
| 7,266,412 B2 | 7/2007 | Stypulkowski | |
| 7,299,085 B2 | 11/2007 | Bergelson et al. | |
| 7,359,751 B1 | 4/2008 | Erickson et al. | |
| 7,373,204 B2 | 5/2008 | Gelfand et al. | |
| 7,440,806 B1 | 10/2008 | Whitehurst et al. | |
| 7,452,336 B2 | 11/2008 | Thompson | |
| 7,463,927 B1 | 12/2008 | Chaouat | |
| 7,474,223 B2 | 1/2009 | Nycz et al. | |
| 7,481,759 B2 | 1/2009 | Whitehurst et al. | |
| 7,489,970 B2 | 2/2009 | Lee et al. | |
| 7,496,403 B2 | 2/2009 | Cao et al. | |
| 7,499,048 B2 | 3/2009 | Sieracki et al. | |
| 7,505,815 B2 | 3/2009 | Lee et al. | |
| 7,551,960 B2 | 6/2009 | Forsberg et al. | |
| 7,602,384 B2 | 10/2009 | Rosenberg et al. | |
| 7,617,002 B2 | 11/2009 | Goetz | |
| 7,627,372 B2 | 12/2009 | Vaisnys et al. | |
| 7,640,059 B2 | 12/2009 | Forsberg et al. | |
| 7,657,317 B2 | 2/2010 | Thacker et al. | |
| 7,685,005 B2 | 3/2010 | Riff et al. | |
| 7,711,603 B2 | 5/2010 | Vanker et al. | |
| 7,720,549 B2 | 5/2010 | Schroeppel et al. | |
| 7,747,330 B2 | 6/2010 | Nolan et al. | |
| 7,778,710 B2 | 8/2010 | Propato | |
| 7,801,596 B2 | 9/2010 | Fischell et al. | |
| 7,801,611 B2 | 9/2010 | Persen et al. | |
| 7,805,199 B2 | 9/2010 | KenKnight et al. | |
| 7,774,067 B2 | 10/2010 | Keacher et al. | |
| 7,822,483 B2 | 10/2010 | Stone et al. | |
| 7,826,901 B2 * | 11/2010 | Lee | A61N 1/36082 128/903 |
| 7,853,323 B2 | 12/2010 | Goetz | |
| 7,885,712 B2 | 2/2011 | Goetz et al. | |
| 7,890,180 B2 | 2/2011 | Quiles et al. | |
| 7,928,995 B2 | 4/2011 | Daignault | |
| 7,934,508 B2 | 5/2011 | Behm | |
| 7,940,933 B2 | 5/2011 | Corndorf | |
| 7,953,492 B2 | 5/2011 | Corndorf | |
| 7,953,612 B1 | 5/2011 | Palmese et al. | |
| 7,957,808 B2 | 6/2011 | Dawant et al. | |
| 7,978,062 B2 | 7/2011 | LaLonde et al. | |
| 7,991,482 B2 | 8/2011 | Bradley | |
| 8,014,863 B2 | 9/2011 | Zhang et al. | |
| 8,021,298 B2 | 9/2011 | Baird et al. | |
| 8,027,726 B2 | 9/2011 | Ternes | |
| 8,046,241 B1 | 10/2011 | Dodson | |
| 8,060,216 B2 | 11/2011 | Greenberg et al. | |
| 8,068,915 B2 | 11/2011 | Lee et al. | |
| 8,068,918 B2 | 11/2011 | Vallapureddy et al. | |
| 8,078,440 B2 | 12/2011 | Otto et al. | |
| 8,082,162 B2 | 12/2011 | Flood | |
| 8,121,702 B2 | 2/2012 | King | |
| 8,135,566 B2 | 3/2012 | Marshall et al. | |
| 8,140,160 B2 | 3/2012 | Pless et al. | |
| 8,140,167 B2 | 3/2012 | Donders et al. | |
| 8,160,328 B2 | 4/2012 | Goetz et al. | |
| 8,160,704 B2 | 4/2012 | Freeberg | |
| 8,165,385 B2 | 4/2012 | Reeves et al. | |
| 8,187,015 B2 | 5/2012 | Boyd et al. | |
| 8,200,324 B2 | 6/2012 | Shen et al. | |
| 8,200,340 B2 | 6/2012 | Skelton et al. | |
| 8,219,206 B2 | 7/2012 | Skelton et al. | |
| 8,233,991 B2 | 7/2012 | Woods et al. | |
| 8,246,680 B2 | 8/2012 | Betz et al. | |
| 8,249,713 B2 | 8/2012 | Fang et al. | |
| 8,255,060 B2 | 8/2012 | Goetz et al. | |
| 8,323,218 B2 | 12/2012 | Davis et al. | |
| 8,326,433 B2 | 12/2012 | Blum et al. | |
| 8,340,775 B1 | 12/2012 | Cullen et al. | |
| 8,382,666 B1 | 2/2013 | Mao et al. | |
| 8,386,032 B2 | 2/2013 | Bachinski et al. | |
| 8,401,666 B2 | 3/2013 | Skelton et al. | |
| 8,428,727 B2 | 4/2013 | Bolea et al. | |
| 2001/0037220 A1 | 11/2001 | Merry et al. | |
| 2003/0076301 A1 | 4/2003 | Tsuk et al. | |
| 2003/0107572 A1 | 6/2003 | Smith et al. | |
| 2003/0139652 A1 | 7/2003 | Kang et al. | |
| 2003/0171911 A1 | 7/2003 | Fairweather | |
| 2003/0177031 A1 | 9/2003 | Malek | |
| 2004/0088374 A1 | 5/2004 | Webb et al. | |
| 2004/0122477 A1 | 6/2004 | Whitehurst et al. | |
| 2004/0210273 A1 | 10/2004 | Wang | |
| 2005/0107831 A1 | 5/2005 | Hill et al. | |
| 2005/0149356 A1 | 7/2005 | Cyr et al. | |
| 2005/0168460 A1 | 8/2005 | Razdan et al. | |
| 2005/0277872 A1 | 12/2005 | Colby et al. | |
| 2006/0089888 A1 | 4/2006 | Roger | |
| 2006/0100832 A1 | 5/2006 | Bowman | |

(56) References Cited

U.S. PATENT DOCUMENTS

| | | |
|---|---|---|
| 2006/0241720 A1 | 10/2006 | Woods et al. |
| 2006/0242159 A1 | 10/2006 | Bishop et al. |
| 2006/0282168 A1 | 12/2006 | Sherman et al. |
| 2007/0078497 A1 | 4/2007 | Vandanacker |
| 2007/0093998 A1 | 4/2007 | El-Baroudi et al. |
| 2007/0179349 A1 | 8/2007 | Hoyme et al. |
| 2007/0203537 A1 | 8/2007 | Goetz et al. |
| 2007/0203538 A1 | 8/2007 | Stone et al. |
| 2007/0203543 A1 | 8/2007 | Stone et al. |
| 2007/0213790 A1 | 9/2007 | Nolan et al. |
| 2008/0004675 A1 | 1/2008 | King et al. |
| 2008/0033303 A1 | 2/2008 | Wariar et al. |
| 2008/0046036 A1 | 2/2008 | King et al. |
| 2008/0140161 A1 | 6/2008 | Goetz et al. |
| 2008/0177362 A1 | 7/2008 | Phillips et al. |
| 2008/0218517 A1 | 9/2008 | Holmdahl |
| 2008/0262565 A1 | 10/2008 | Bentwich |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0136094 A1 | 2/2009 | Driver et al. |
| 2009/0089034 A1 | 4/2009 | Penney et al. |
| 2009/0099624 A1 | 4/2009 | Kokones et al. |
| 2009/0132009 A1 | 5/2009 | Torgenson et al. |
| 2009/0196471 A1 | 8/2009 | Goetz et al. |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0038498 A1 | 1/2011 | Edgar |
| 2011/0023343 A1 | 2/2011 | Turner et al. |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennet et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0224523 A1 | 9/2011 | Burdiman |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0136409 A1* | 5/2012 | Goetz ............... A61N 1/36071 607/45 |
| 2012/0192874 A1 | 8/2012 | Bolea et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Connor et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| WO | WO 9959106 | 11/1999 |
| WO | WO 2002009808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Boston Scientific Corporation, "Boston Scientific Precision Spectra System Programming Manual", Copyright 2010, 580 pgs.

\* cited by examiner

METHOD AND SYSTEM OF BRACKETING STIMULATION PARAMETERS ON CLINICIAN PROGRAMMERS

PRIORITY DATA

The present application is a utility application of provisional U.S. Patent Application No. 61/695,700, filed on Aug. 31, 2012, entitled "Method and System of Bracketing Stimulation Parameters On Clinician Programmers," and a utility application of provisional U.S. Patent Application No. 61/824,296, filed on May 16, 2013, entitled "Features and Functionalities of an Advanced Clinician Programmer," the disclosures of each of which are hereby incorporated by reference in their entirety.

BACKGROUND

As medical device technologies continue to evolve, active implanted medical devices have gained increasing popularity in the medical field. For example, one type of implanted medical device includes neurostimulator devices, which are battery-powered or battery-less devices designed to deliver electrical stimulation to a patient. Through proper electrical stimulation, the neurostimulator devices can provide pain relief for patients or restore bodily functions.

Implanted medical devices (for example, a neurostimulator) can be controlled using an electronic programming device such as a clinician programmer or a patient programmer. These programmers can be used by medical personnel or the patient to define the particular electrical stimulation therapy to be delivered to a target area of the patient's body, to alter one or more parameters of the electrical stimulation therapy, or otherwise to conduct communications with a patient.

Despite many advances made in the field of neurostimulation, one drawback is that the electronic programmers such as the clinician programmer rely on manual programming of stimulation parameters. For example, in a typical programming session, a healthcare professional manually sets the electrical stimulation parameters (e.g., amplitude, frequency, pulse width, etc.), tests them with the patient, receives patient feedback, and then manually programs new electrical stimulation parameters until the patient feels maximum pain relief. The manual programming (and reprogramming) of the electrical stimulation parameters is time consuming, and the comparison between two similarly programmed pulses may be difficult when too much time is spent reprogramming between the trials of the pulses.

Therefore, although existing electronic programmers used for neurostimulation have been generally adequate for their intended purposes, they have not been entirely satisfactory in every aspect.

SUMMARY

One aspect of the present disclosure involves an electronic apparatus for setting stimulation parameters of a neurostimulator to deliver neurostimulation to a patient. The electronic device includes: a memory storage component configured to store programming code; and a computer processor configured to execute the programming code to perform the following tasks: displaying a plurality of stimulation parameters available for bracketing, the stimulation parameters being selected from the group consisting of: stimulation current amplitude, pulse width, frequency, and contact location; selecting, in response to an input from a user, at least a subset of the stimulation parameters for bracketing; obtaining a respective initial value for each of the stimulation parameters in the selected subset; generating, through a bracketing process, a plurality of bracketed values for each of the stimulation parameters in the selected subset, wherein the bracketed values are generated as a function of the initial value; and automatically programming the neurostimulator to deliver a plurality of stimulation pulses to the patient, wherein a different combination of the bracketed values is programmed into the neurostimulator for each stimulation pulse.

Another aspect of the present disclosure involves a medical system. The medical system includes: a neuro stimulator configured to deliver electrical stimulation to a patient via one or more of a plurality of contacts located on a lead; and a portable electronic programmer having an electronic processor and a touch-sensitive graphical user interface, wherein the electronic programmer is configured to: display, through the touch-sensitive graphical user interface, a plurality of stimulation parameters available for bracketing, the stimulation parameters being selected from the group consisting of: stimulation current amplitude, pulse width, frequency, and contact location; select, in response to a user input received through the touch-sensitive graphical user interface, at least a subset of the stimulation parameters for bracketing; obtain a respective initial value for each of the stimulation parameters in the selected subset; generate, through a bracketing process performed by the electronic processor, a plurality of bracketed values for each of the stimulation parameters in the selected subset, wherein the bracketed values are generated as a function of the initial value; and program, without requiring any user input, the neurostimulator to deliver a plurality of stimulation pulses to the patient, wherein a different combination of the bracketed values is programmed into the neurostimulator for each stimulation pulse.

Yet another aspect of the present disclosure involves a method of setting stimulation parameters for neurostimulation. The method comprises: displaying a plurality of stimulation parameters available for bracketing, the stimulation parameters being selected from the group consisting of: stimulation current amplitude, pulse width, frequency, and contact location; selecting, in response to an input from a user, at least a subset of the stimulation parameters for bracketing; obtaining a respective initial value for each of the stimulation parameters in the selected subset; generating, through a bracketing process, a plurality of bracketed values for each of the stimulation parameters in the selected subset, wherein the bracketed values are generated as a function of the initial value; and delivering a plurality of stimulation pulses to a patient through a neurostimulator that is automatically programmed with a different combination of the bracketed values for the stimulation parameters for each stimulation pulse.

One more aspect of the present disclosure involves an electronic apparatus for setting stimulation parameters of a neurostimulator to deliver neurostimulation. The electronic apparatus comprises: input/output means for communicating with a user, the input/output means including a touch-sensitive screen configured to detect an input from the user and display an output to the user; memory storage means for storing executable instructions; and computer processor means for executing the instructions to perform the following tasks: displaying a plurality of stimulation parameters available for bracketing, the stimulation parameters being selected from the group consisting of: stimulation current amplitude, pulse width, frequency, and contact location;

selecting, in response to an input from a user, at least a subset of the stimulation parameters for bracketing; obtaining a respective initial value for each of the stimulation parameters in the selected subset; generating, through a bracketing process, a plurality of bracketed values for each of the stimulation parameters in the selected subset, wherein the bracketed values are generated as a function of the initial value; and automatically programming, without requiring user input, the neurostimulator to deliver a plurality of stimulation pulses to the patient, wherein a different combination of the bracketed values is programmed into the neurostimulator for each stimulation pulse.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

The use of active implanted medical devices has become increasingly prevalent over time. Some of these implanted medical devices include neurostimulator devices that are capable of providing pain relief by delivering electrical stimulation to a patient. In that regards, electronic programmers have been used to configure or program these neurostimulators (or other types of suitable active implanted medical devices) so that they can be operated in a certain manner. These electronic programmers include clinician programmers and patient programmers, each of which may be a handheld device. For example, a clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

In recent years, these electronic programmers have achieved significant improvements, for example, improvements in size, power consumption, lifetime, and ease of use. Despite these advances, the capabilities of electronic programmers have not been fully exploited, for example, in terms of setting stimulation programming parameters. Currently, electronic programmers can be used by healthcare professionals to manually program a set of stimulation parameters for a neurostimulator for each stimulation pulse. A plurality of stimulation pulses may be programmed to test the efficacy of each pulse. As such, the manual nature of the stimulation pulse programming can be time-consuming and tedious. If patient feedback is needed in response to each stimulation pulse, a lengthy delay (caused by the manual programming) between the pulses may decrease the accuracy of the comparison, as the patient may forget how effective a previous stimulation pulse was in terms of treating his/her pain. In addition, patient feedback is only received verbally from the patient in most cases. This may further increase the delay as the patient has to verbally describe how he/she feels.

To address the issues discussed above, the present disclosure offers a method and system of automatically programming stimulation parameters via a bracketing process that is performed by an electronic programmer such as the clinician programmer, as discussed below in more detail.

Figure 1:
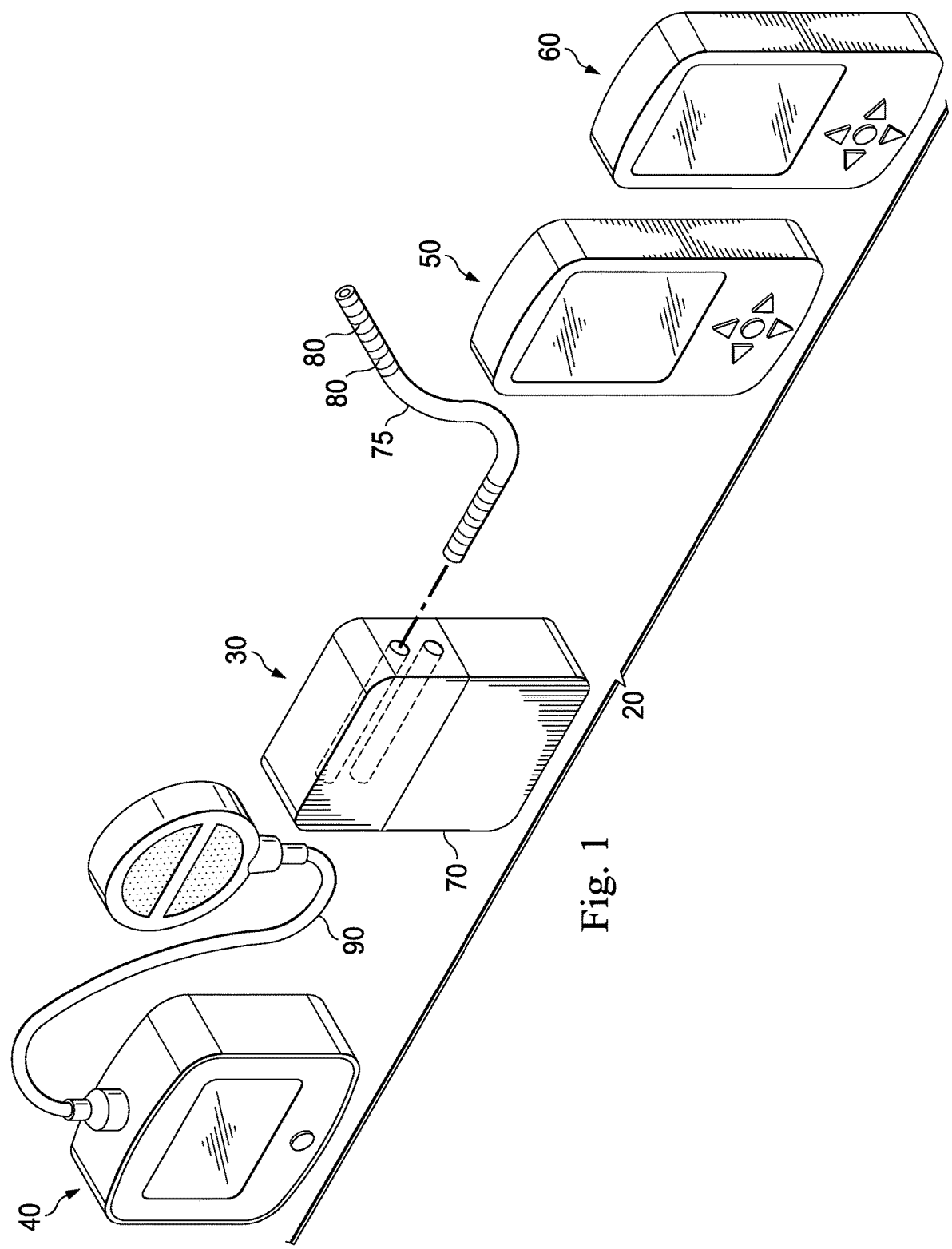
FIG. 1 is a simplified block diagram of an example medical environment in which evaluations of a patient may be conducted according to various aspects of the present disclosure.

FIG. 1 is a simplified block diagram of a medical device system 20 is illustrated to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end (referred to as a connection end) of one or more percutaneous, or skin-penetrating, leads. The other end (referred to as a stimulating end) of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer. However, it is understood that the electronic programmer may also be the patient programmer 50 or other touch screen programming devices (such as smart-phones or tablet computers) in other embodiments.

FIGS. 2-4 and 6-8 illustrate an example user interface 100 of an embodiment of the clinician programmer 60. The interface 100 is displayed on a touch-sensitive screen of the clinician programmer and allows for interactive input/output for a target user, which may be a healthcare professional, for example, a surgeon. The user and the healthcare professional are interchangeably referred in the following paragraphs, but it is understood that they need not necessarily be the same entity.

Figure 2:
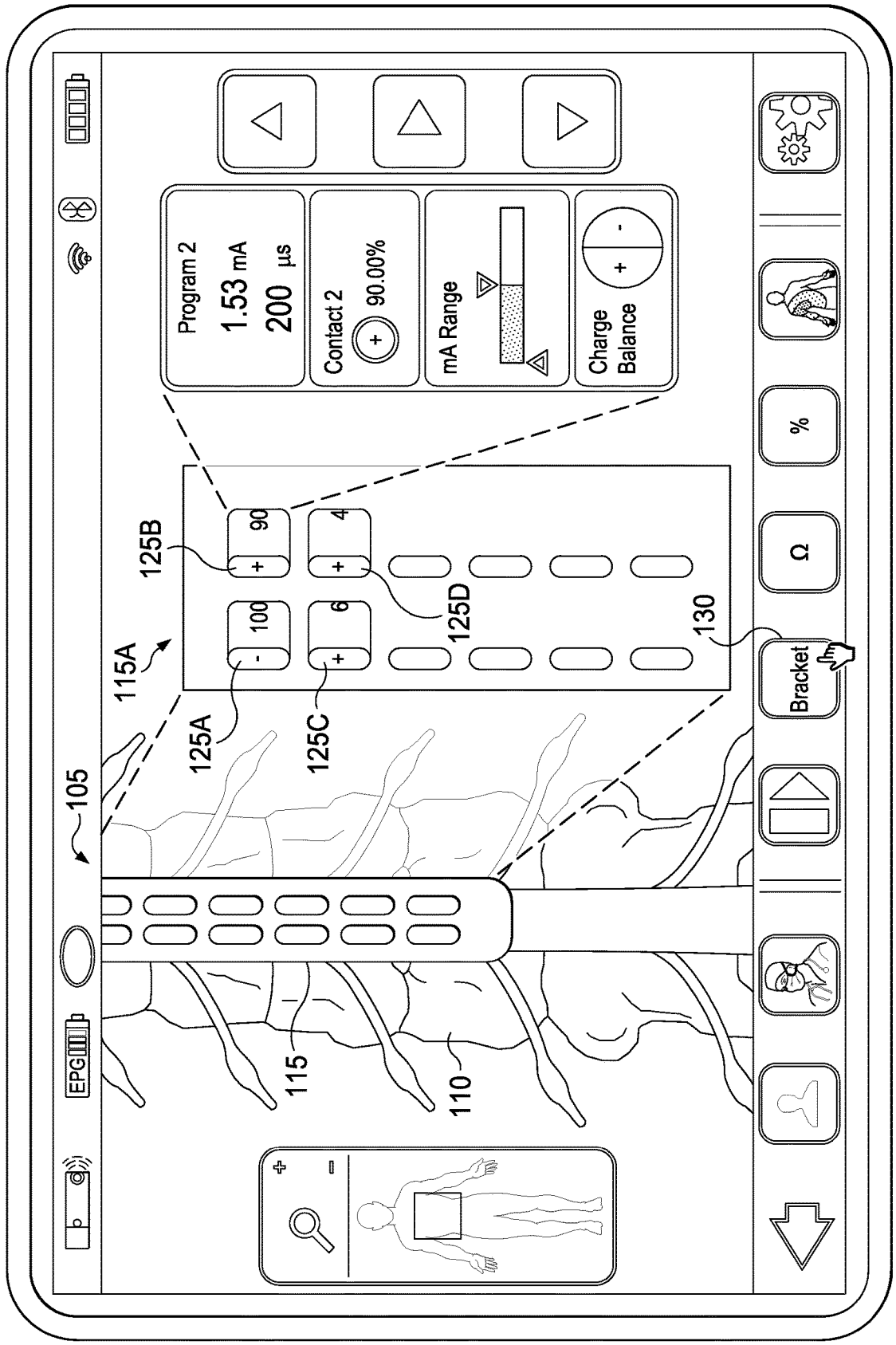
FIGS. 2-4 and 6-8 are embodiments of a user interface for bracketing electrical stimulation parameters according to various aspects of the present disclosure.

Referring to FIG. 2, the user interface 100 displays a virtual representation of an anatomical environment 105 in which a lead is implanted. In the illustrated embodiment, the anatomical environment 105 includes a virtual representation of a portion of a spine 110 (representing the spine of the patient), as well as a virtual representation of a lead 115 shown with respect to the spine 110. The lead 115 may be an embodiment of the lead 75 shown in FIG. 1, or any other suitable implantable lead. The anatomical environment 105 may include a virtual representation of an implantable pulse generator 120 (not specifically illustrated herein) as an embodiment of the implantable medical device 30 shown in FIG. 1.

The user interface 100 also illustrates another virtual representation of the lead 115A in greater detail. For example, the lead 115A is a 2×6 lead and contains two columns and six rows of electrodes 125 (also interchangeably referred to as contacts or electrode contacts herein). Each of the electrodes 125 can be individually programmed with its own set of stimulation parameters in order to deliver electrical stimulation to a nearby nerve tissue. These stimulation parameters include, but are not limited to, electrical current amplitude, pulse width, frequency, electrode location and electrode polarity (anode/cathode).

Through the user interface 100, a user may manually program stimulation parameters for one or more of the electrodes 125, for example, the electrode 125B to generate a test stimulation pulse, for example in accordance with U.S. patent application Ser. No. 13/601,631, filed on Aug. 31, 2012, and entitled "Programming and Virtual Reality Representation of Stimulation Parameter Groups" to Norbert Kaula, et al., the contents of which are hereby incorporated by reference in its entirety. However, such manual programming of the electrodes 125 can be time-consuming, and if multiple test stimulation pulses are needed, each one would require its own manual programming session. This may frustrate both the user and the patient in a clinical setting where the user has to experiment with different stimulation pulses to see which one would offer the most pain reduction for the patient. Alternatively, the user may choose not to exhaustively search for the optimum solutions due to the time constraints, in which case the patient may not be offered the best treatment potentially available.

According to the present disclosure, a stimulation parameter bracketing process is performed by the clinician programmer 60 to allow for automatic population of the stimulation parameters, thereby quickly generating the desired test stimulation pulses. For example, the user interface 100 contains a virtual icon or button 130, which reads "Bracket" in the illustrated embodiment. Upon being pressed by a user, the virtual icon 130 will trigger the display of a list of stimulation parameters that are available for bracketing for an activated electrode, for example electrode 125B. Of course, the user may select any of the other electrodes 125 for bracketing.

Figure 3:
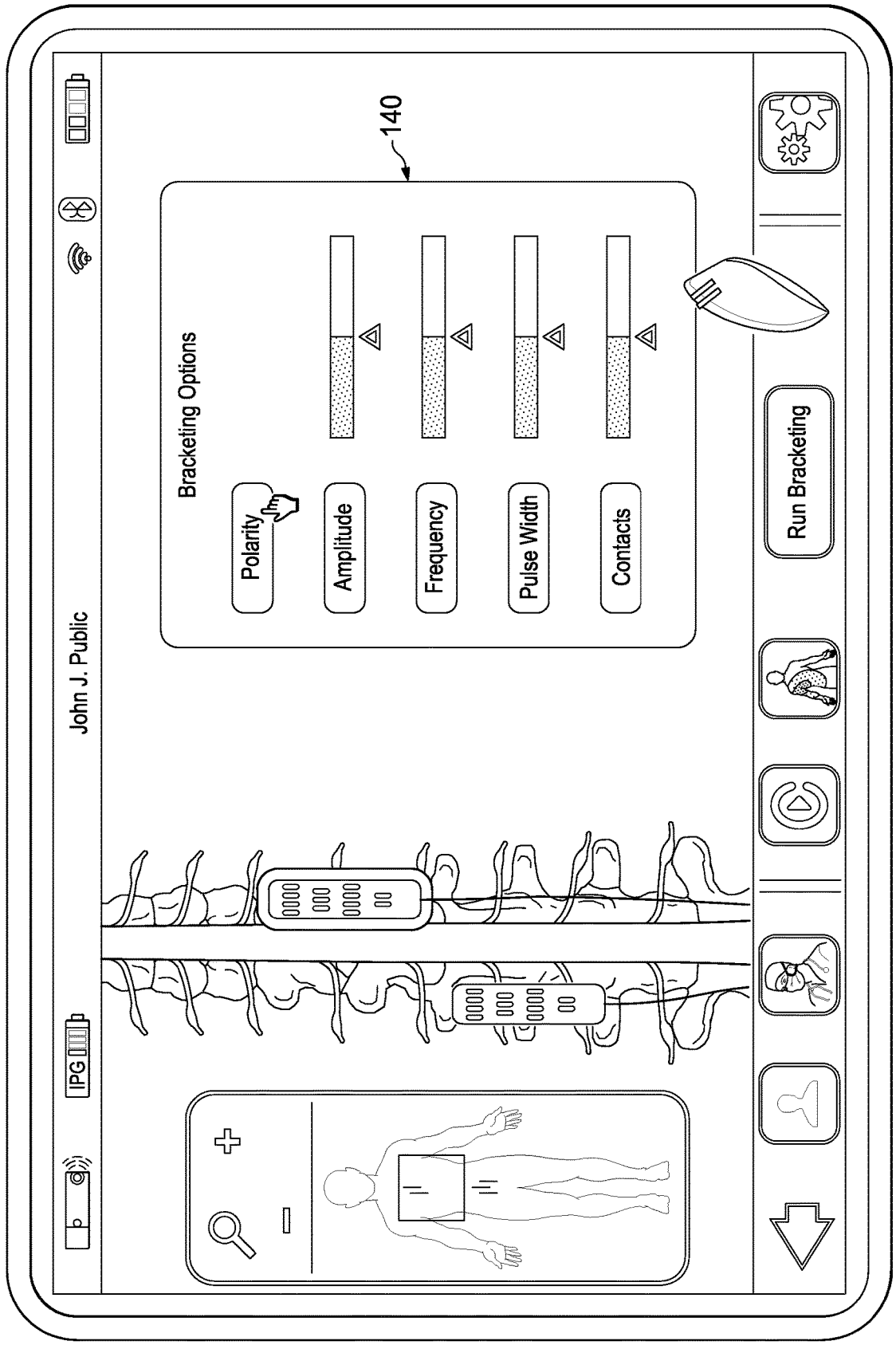

Referring to FIG. 3, the list of stimulation parameters available for bracketing is displayed in the user interface 100 according to an embodiment. The user interface 100 includes a menu 140 of bracketing options, in which shows "Polarity" "Amplitude" "Frequency" "Pulse Width" and "Contacts" as the list of stimulation parameters available for bracketing. Bracketing is a process or method of automatically generating a range of values as a function of an initial value. In an embodiment, based on an initial value of $X_{1initial}$, and based on a bracketing step size, a bracketing process may generate $X_1, X_2, X_3, \ldots X_n$, where each of $X_1, X_2, X_3, \ldots X_n$ is mathematically derived from $X_{initial}$. In some embodiments, $X_1, X_2, X_3, \ldots X_n$ may each be offset from $X_{initial}$ by an integer multiple of the step size. For example, if $X_{initial}$ is set to 100, and the bracketing step size is set to 10, then $X_1, X_2, X_3$ and $X_4$ may be 80, 90, 110, and 120, respectively. $X_{initial}$ may also be considered part of the bracketed values, and may be the median among these bracketed values in this example. However, it is understood that in other embodiments, the initial value $X_{initial}$ may not necessarily be the median of the bracketed values, and the bracketed values may not necessarily be offset from $X_{initial}$ by an integer multiple of the step size. For example, with an $X_{initial}$ value of 100, $X_1, X_2, X_3$ and $X_4$ may be set to 90, 95, 110, and 120, respectively, or even 95, 105, 110, and 120, respectively.

In some embodiments, the initial value of each stimulation parameter to be bracketed is set before the bracketing options menu 140 is displayed. For example, the initial values for the stimulation parameters may be manually set by the user (e.g., healthcare professional) through the user interface 100, based on the user's personal knowledge and experience with the patient and the neurostimulator. In other embodiments, the initial values for the stimulation parameters may be calculated by a Computer Assisted Stimulation Programming (CASP) technique. Various embodiments of the CASP technique are disclosed in U.S. patent application Ser. No. 13/118,764, filed on May 31, 2011, entitled "System And Method Of Establishing A Protocol For Providing Electrical Stimulation With a Stimulation System To Treat A Patient" to Kaula, et al., and to provisional U.S. Patent Application No. 61/824,296, filed on May 16, 2013, entitled "Features and Functionalities of an Advanced Clinician Programmer" to Kaula et al., the disclosures of each of which are hereby incorporated by reference in their entirety.

In other embodiments, the initial value of each stimulation parameter to be bracketed may be manually specified by the user, which may be different from the values shown in FIG. 2.

Figure 4:
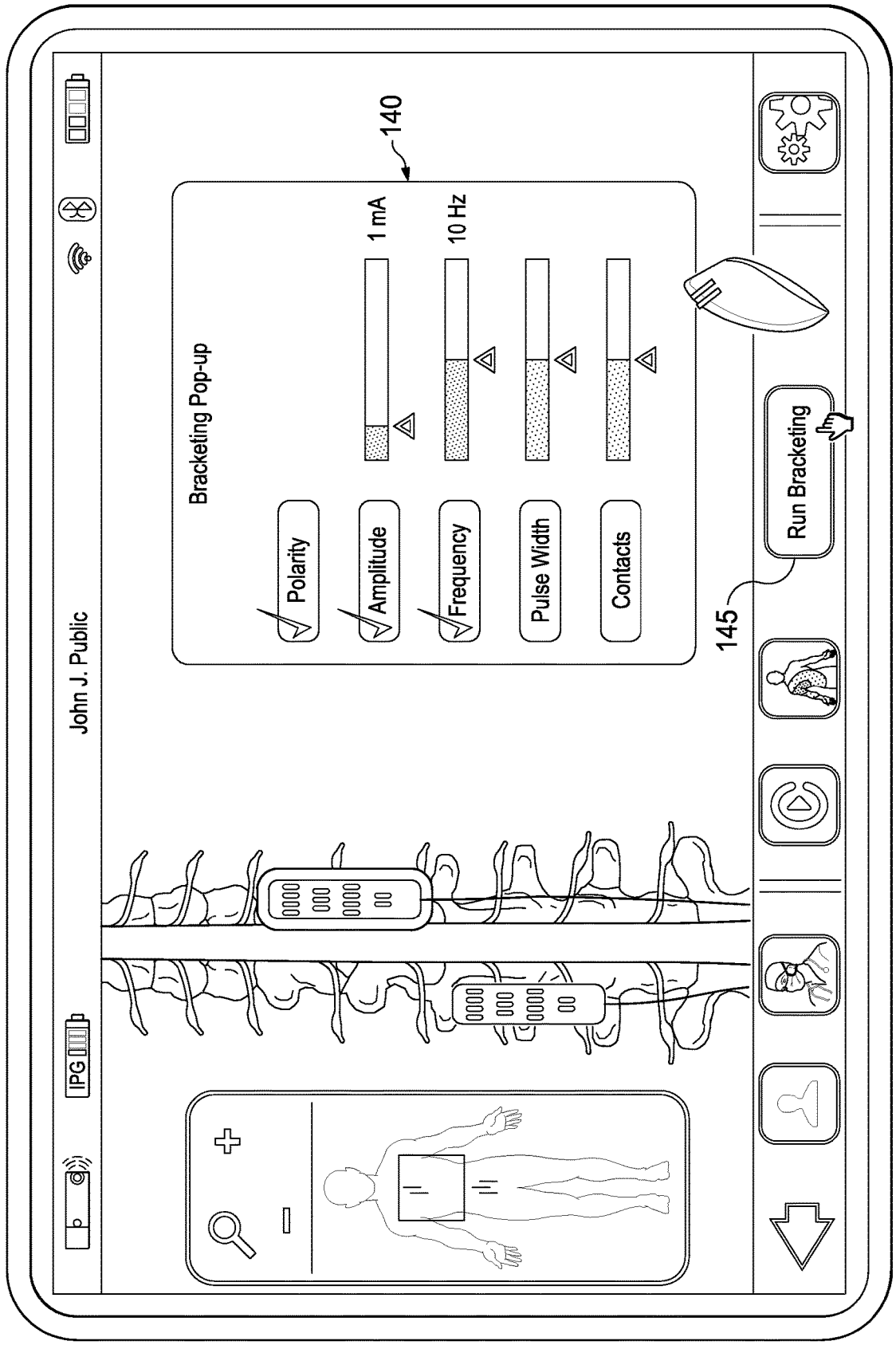

Referring now to FIG. 4, the user may select a subset of the stimulation parameters available for bracketing in the bracketing options menu 140. In the embodiment shown, the selected subset of stimulation parameters includes polarity, amplitude, and frequency. The selected subset of stimulation parameters may be highlighted by a check mark or another suitable indicator. Next, the graphical user interface 100 allows the user to set the step size for each of the selected stimulation parameters in the subset. In the embodiment shown, the step size for the amplitude is set to 1 milli-Amp (mA), and the step size for the frequency is set to 10 Hertz (Hz). The electrode polarity includes an anode polarity and a cathode polarity, and its bracketing means that the bracketed values will include both the anode and the cathode.

The pulse width and contacts are not selected for bracketing in the example embodiment shown in FIG. 4, and as such no bracketing will be performed for them. But in embodiments where pulse width and contacts are selected for bracketing, the bracketing for the pulse width may be similar to the bracketing of amplitude and frequency (i.e., by setting an appropriate step size for pulse width), and the bracketing for the contacts may involve moving the location for the activated electrode one or two electrode at a time. For example, had electrode 4 been selected for bracketing, the bracketing process may generate the test pulses at electrodes 3 and 5, or at electrodes 2 and 6.

The user interface 100 includes a virtual "Run Bracketing" button 145. The user may click the "Run Bracketing" button 145 to activate the bracketing process for the activated electrodes, for example, one or more of the electrodes 125 shown in FIG. 2. As discussed above, the bracketing process generates a plurality of bracketed values for each of the stimulation parameters in the selected subset. In some embodiments, these bracketed values may be used to create a bracketing table, for example, Table 1 below.

TABLE 1

| Polarity | Amplitude | Frequency |
| --- | --- | --- |
| Cathode | 5 mA | 100 Hz |
| Cathode | 5 mA | 90 Hz |
| Cathode | 5 mA | 110 Hz |
| Cathode | 6 mA | 100 Hz |
| Cathode | 6 mA | 90 Hz |
| Cathode | 6 mA | 110 Hz |
| Cathode | 4 mA | 100 Hz |
| Cathode | 4 mA | 90 Hz |
| Cathode | 4 mA | 110 Hz |
| Anode | 5 mA | 100 Hz |
| Anode | 5 mA | 90 Hz |
| Anode | 5 mA | 110 Hz |
| Anode | 6 mA | 100 Hz |
| Anode | 6 mA | 90 Hz |
| Anode | 6 mA | 110 Hz |
| Anode | 4 mA | 100 Hz |
| Anode | 4 mA | 90 Hz |
| Anode | 4 mA | 110 Hz |

In the example bracketing table provided above, the stimulation parameters are electrode polarity, amplitude, and frequency. The initial values of these stimulation parameters are set to be cathode, 5 mA, and 100 Hz, respectively. The bracketing step sizes for the amplitude and frequency are set to be 1 mA and 10 Hz, respectively. The electrode polarity does not need a "step size" per se, since its bracketing just means that both an anode and a cathode will be tested. However, in some embodiments, the physical locations for the electrodes can be bracketed as well. For example, the bracketing for the electrodes may be done so that electrodes are "stepped through" from a top of the lead to a bottom of the lead. In that case, the step size for the electrode location bracketing is one electrode location at a time. Alternatively, one or more electrodes may be skipped as the bracketing for the electrodes takes place, in which case the step size is two or more electrodes. It is also understood that the bracketing process may be performed by the user specifying an upper limit and a lower limit for a given parameter, and the range between the upper and lower limits are automatically divided into a plurality of segments. For example, instead of specifying an initial value and a step size for stimulation current amplitude, the user may specify a lower amplitude limit and an upper amplitude limit, and the clinician programmer of the present disclosure will automatically generate a plurality of current amplitudes by dividing the difference between the upper and lower amplitude limits by a given number. That given number (i.e., the denominator) may also be specified by the user in certain embodiments. The stimulation program may be run at each of the generated current amplitude settings.

Based on all the permutations (or combinations) of the bracketed values of the selected stimulation parameters (e.g., shown in Table 1), the clinician programmer 60 will then automatically program the neurostimulator to deliver a plurality of stimulation pulses, where each pulse is automatically programmed with a different combination of the bracketed stimulation parameter values. Using Table 1 as an example, each stimulation pulse is automatically programmed with the stimulation parameter values corresponding to a different row of the table. Thus, stimulation pulse 1 will be automatically programmed to have a cathode electrode polarity for the selected electrode on a lead, the stimulation current amplitude will be automatically programmed to have an amplitude of 5 mA, and a frequency of 100 Hz; stimulation pulse 2 will be automatically programmed to have a cathode electrode polarity for the selected electrode, the stimulation current amplitude will be automatically programmed to have an amplitude of 5 mA, and a frequency of 90 Hz; stimulation pulse 3 will be automatically programmed to have a cathode electrode polarity for the selected electrode, the stimulation current amplitude will be automatically programmed to have an amplitude of 5 mA, and a frequency of 110 Hz; so on and so forth until all the rows of the table 1 have been exhausted. The programming is done without requiring user input. Note that the test stimulation pulses need not necessarily be performed in the same order as shown in Table 1. In other embodiments, one or more of the stimulation parameters may be stepped through from the lowest bracketed value to the highest bracketed value, or vice versa. In addition, for reasons of simplicity, Table 1 above merely illustrates half of what actually takes place on the lead during stimulation. In other words, Table 1 only illustrates the bracketing for either an anode, or a cathode, at any given time. In actuality, current balancing requires the lead to have one or more cathodes to balance out the currents on the anode, and vice versa. Therefore, a Table similar to Table 1 may be constructed for the other electrode(s) that are activated to current-balance the electrodes of Table 1.

Figure 5:
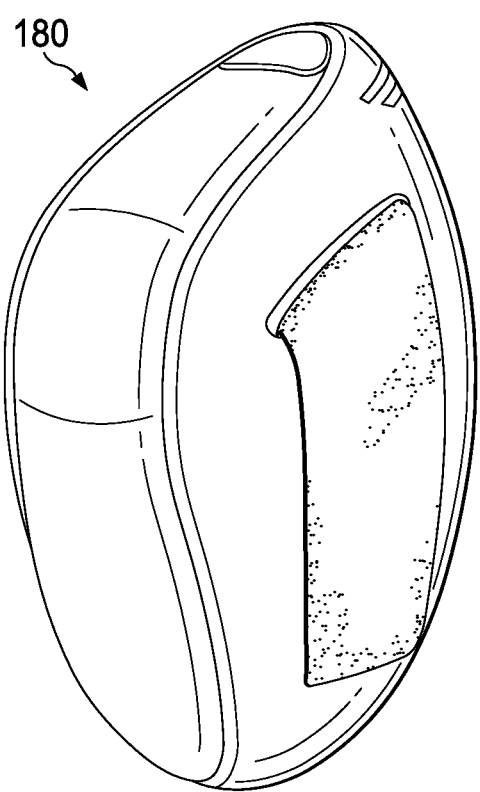
FIG. 5 is a simplified illustration of a portable electronic patient feedback tool according to an embodiment of the present disclosure.
Figure 6:
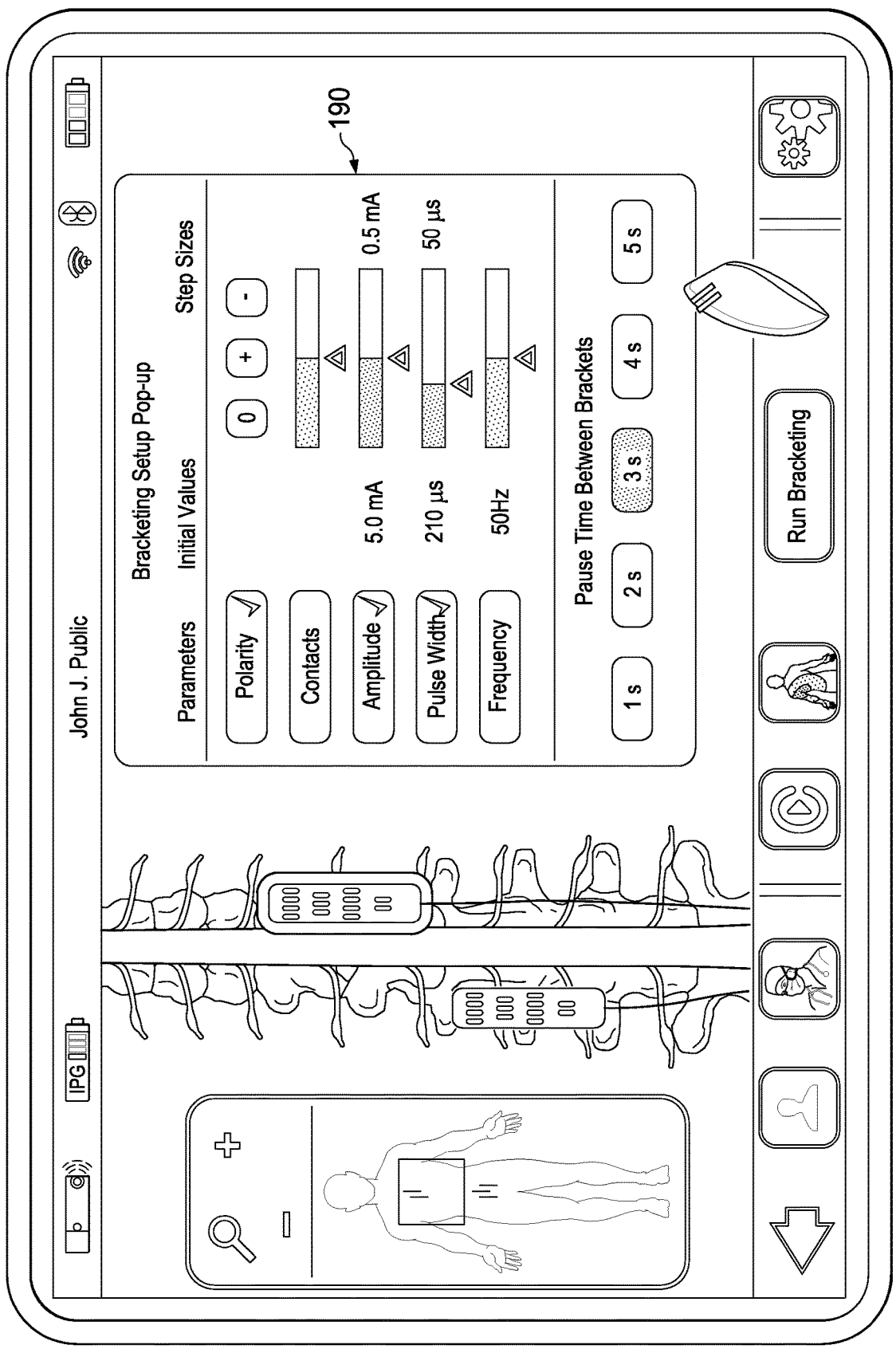

The patient is stimulated by these test stimulation pulses. The present disclosure allows the patient to provide feedback indicating the efficacy of the treatment (e.g., pain reduction while being stimulated by the test pulse). The feedback may be provided either verbally or with a patient feedback tool 180 (PFT), an embodiment of which is illustrated in FIG. 5. The PFT 180 is a portable hand held device and is sensitive to pressure. In some embodiments, the PFT 180 may also be calibrated for each patient before surgery to take into account that particular patient's strength and grip. Additional aspects and other embodiments of the PFT 180 are described in more detail in U.S. Patent Application No. 2012/0310305, filed on May 31, 2011, and entitled "Patient handheld device for use with a spinal cord stimulation system" to Kaula, et al., the disclosure of which is hereby incorporated by reference in its entirety.

The patient may squeeze the PFT 180 more or less to convey the level of pain reduction they experience in response to the delivered electrical stimulation. If the pulse is too intense for the patient, he/she can stop the pulse by applying a hard squeeze to the PFT 180. If a patient senses the pulse covers their area of pain, a light squeeze can be applied to the PFT 180. This non-verbal feedback is used to select a pulse that provides symptom relief for the patient. Note that in some embodiments, the PFT may detect patient inputs other than just pressure (e.g., squeeze). For example, the PFT may detect a gesture from the patient, which may be used to indicate the pain or stimulation experienced by the patient. The patient may also provide verbal feedback. For example, the patient could state, "Pulse A was better than B and C".

In some embodiments, the user interface 100 may allow the user to specify a pause (i.e., time delay) between each pulse. For example, referring to FIG. 6, the user interface 100 includes a bracketing setup pop-up menu 190 in which the pause time between the stimulation pulses (i.e., the "brackets") can be set by a user. The pause gives the patient sufficient time to give feedback with respect to the efficacy of treatment offered by each test stimulation pulse. In other embodiments, the stimulation pulses may be run consecutively without pauses in between. In some of these embodiments, a subsequent stimulation pulse begins only after a patient feedback for a previous test pulse has been detected.

The feedback provided by the patient is used to assign a score to the bracketing pulses. Based on these scores, a set of pulses will be identified that provided the patient with pain relief. These identified pulses may then be run again to determine a single pulse or a reduced number of pulses that provide the best pain relief for the patient. In some embodiments, one or more of these "optimal" stimulation pulses will be automatically recommended to the user through the user interface 100.

Figure 7:
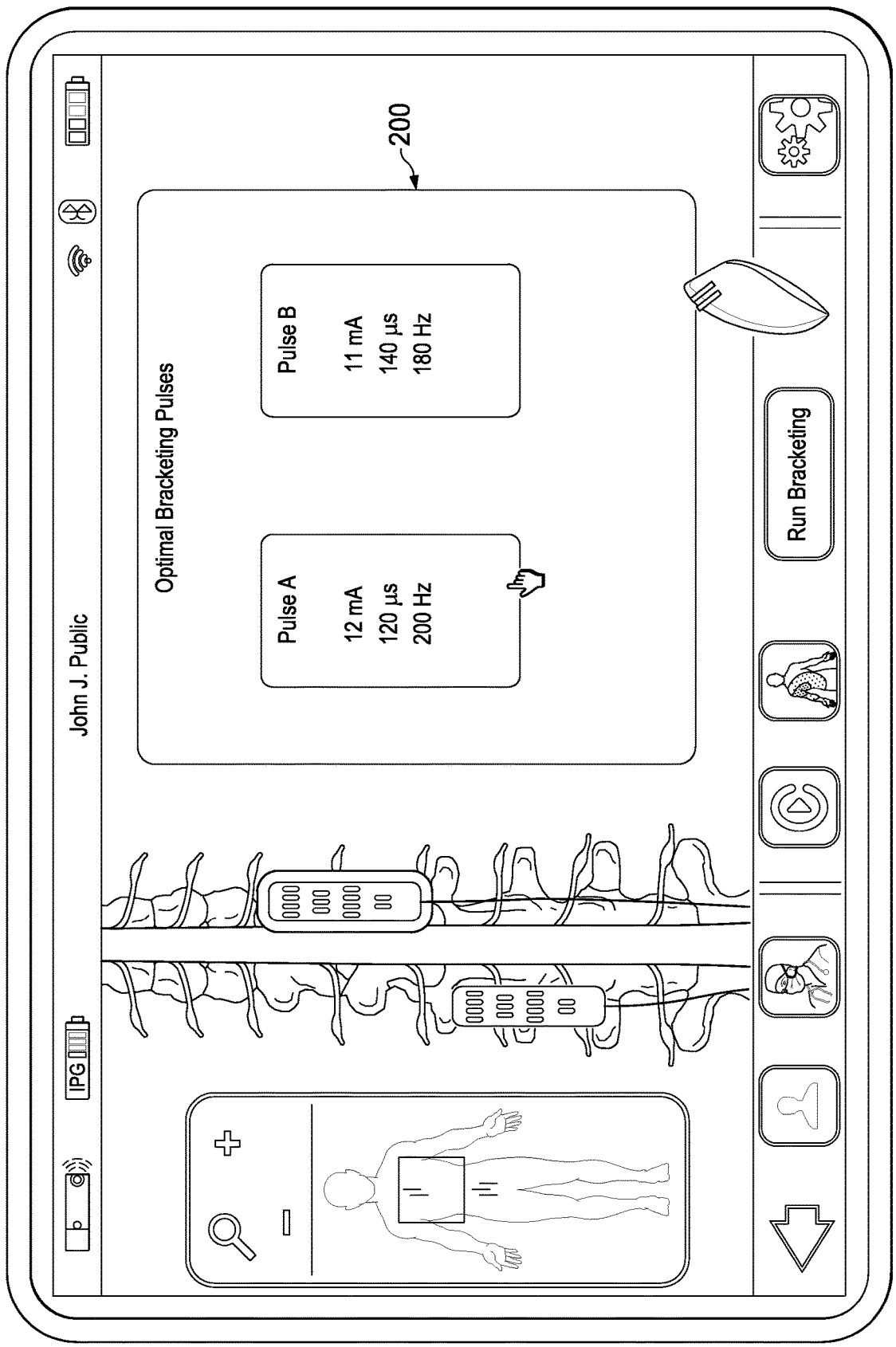

These recommended pulses will then be displayed to the user in FIG. 7, for example, in a menu 200 of the user interface 100. In this example, two example pulses (Pulse A and Pulse B) are displayed, each with its own set of stimulation parameter values obtained from bracketing. Again, these stimulation parameter values are each obtained through a bracketing process discussed above.

Figure 8:
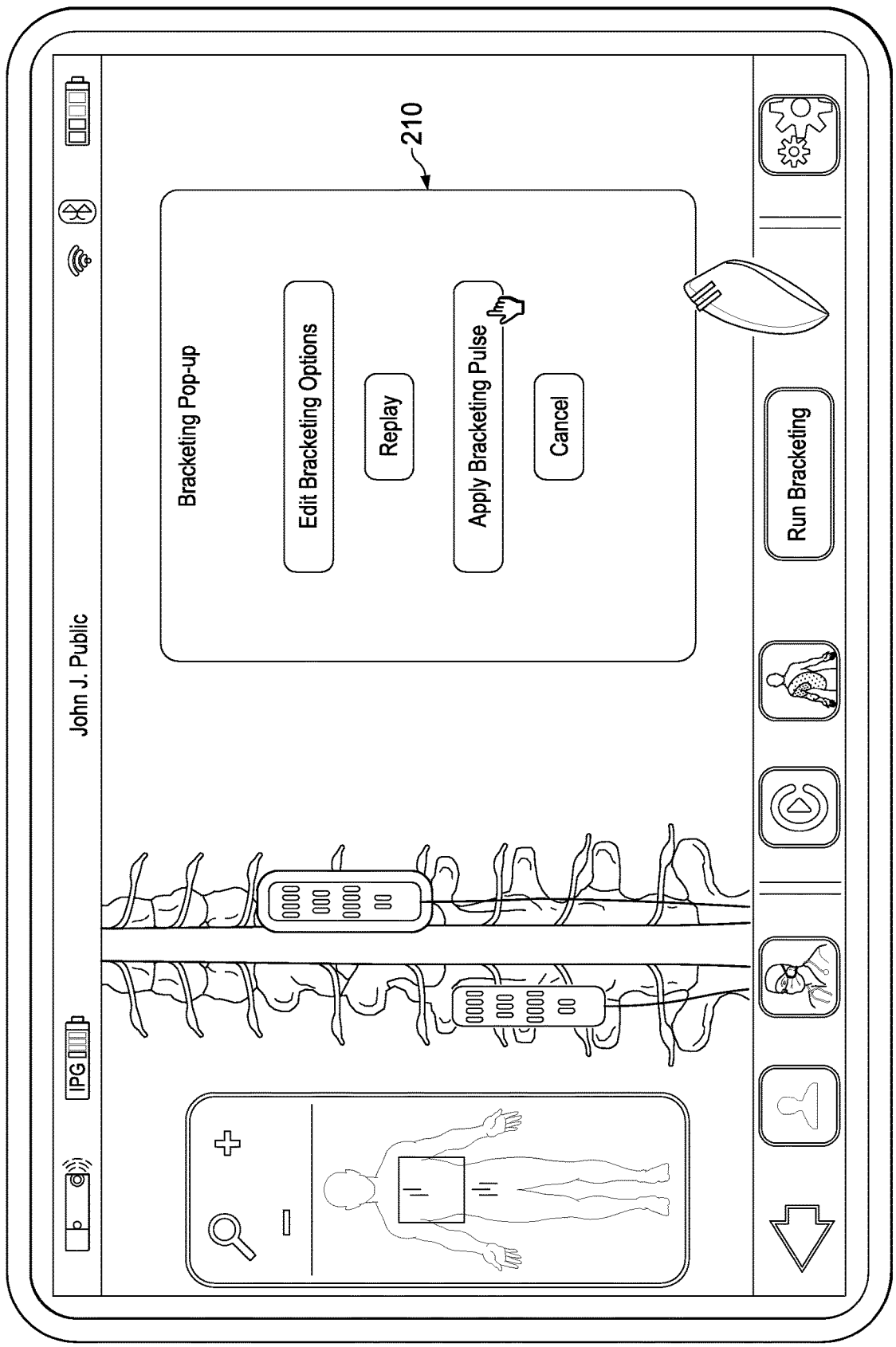

The user may select one of the pulses, which will then trigger the display of another pop-up menu that offers the user more options, for example, the menu 210 shown in FIG. 8. In the embodiment shown in FIG. 8, the menu 210 displays the four following choices: edit the bracketing options, replay the same test pulses, apply the bracketing pulses, and cancel (which allows the user to return to the programming screen of FIG. 2).

It is understood that the bracketing process as discussed above may be done for one electrode, or for multiple electrodes simultaneously.

Figure 9:
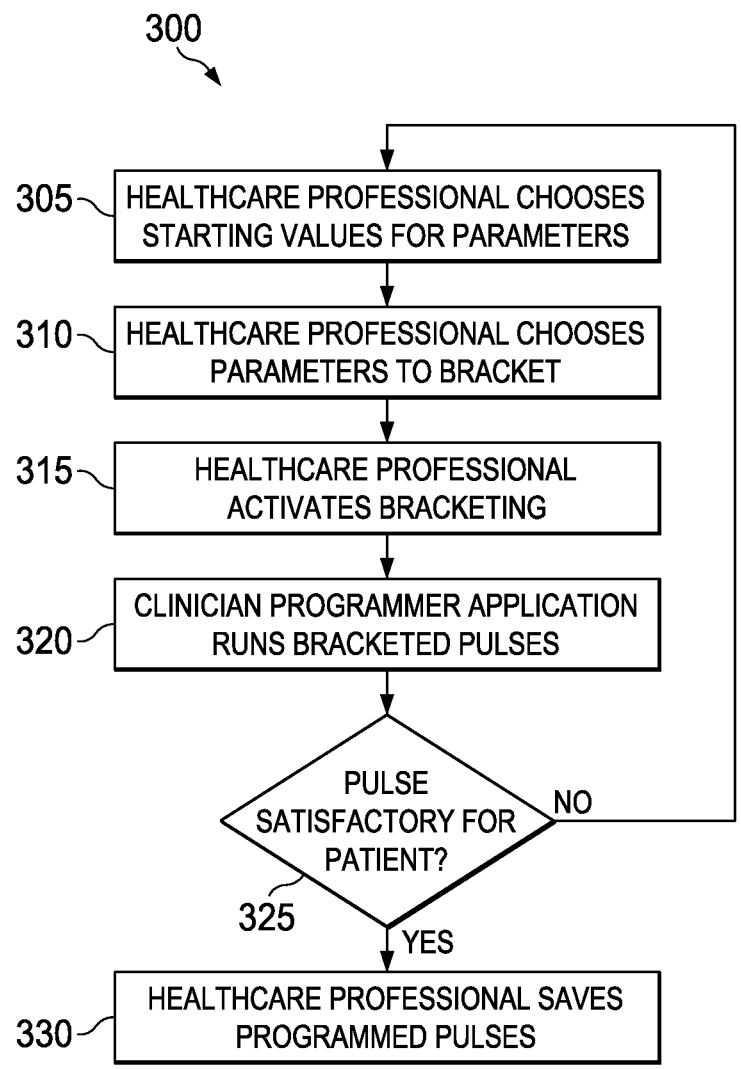
FIGS. 9-11 are simplified flowcharts illustrating a method of bracketing electrical stimulation parameters according to various aspects of the present disclosure.

FIG. 9 is a simplified flowchart of a method 300 of testing stimulation parameters according to the various aspects of the present disclosure. The method 300 includes a step 305, in which a healthcare professional chooses starting values for stimulation parameters. The method 300 proceeds to a step 310, in which the healthcare professional chooses stimulation parameters to bracket. The method 300 proceeds to a step 315, in which the healthcare professional activates bracketing. The method 300 proceeds to a step 320, in which the clinician programmer application runs the bracketed pulses. The method 300 then proceeds to a decision step 325 to determine whether the pulse is satisfactory for the patient. If the answer from the decision step 325 is no, then the method 300 loops back to step 305. On the other hand, if the answer from the decision step 325 is yes, then the method 300 proceeds to a step 330, in which the healthcare professional saves the programmed pulses.

Figure 10:
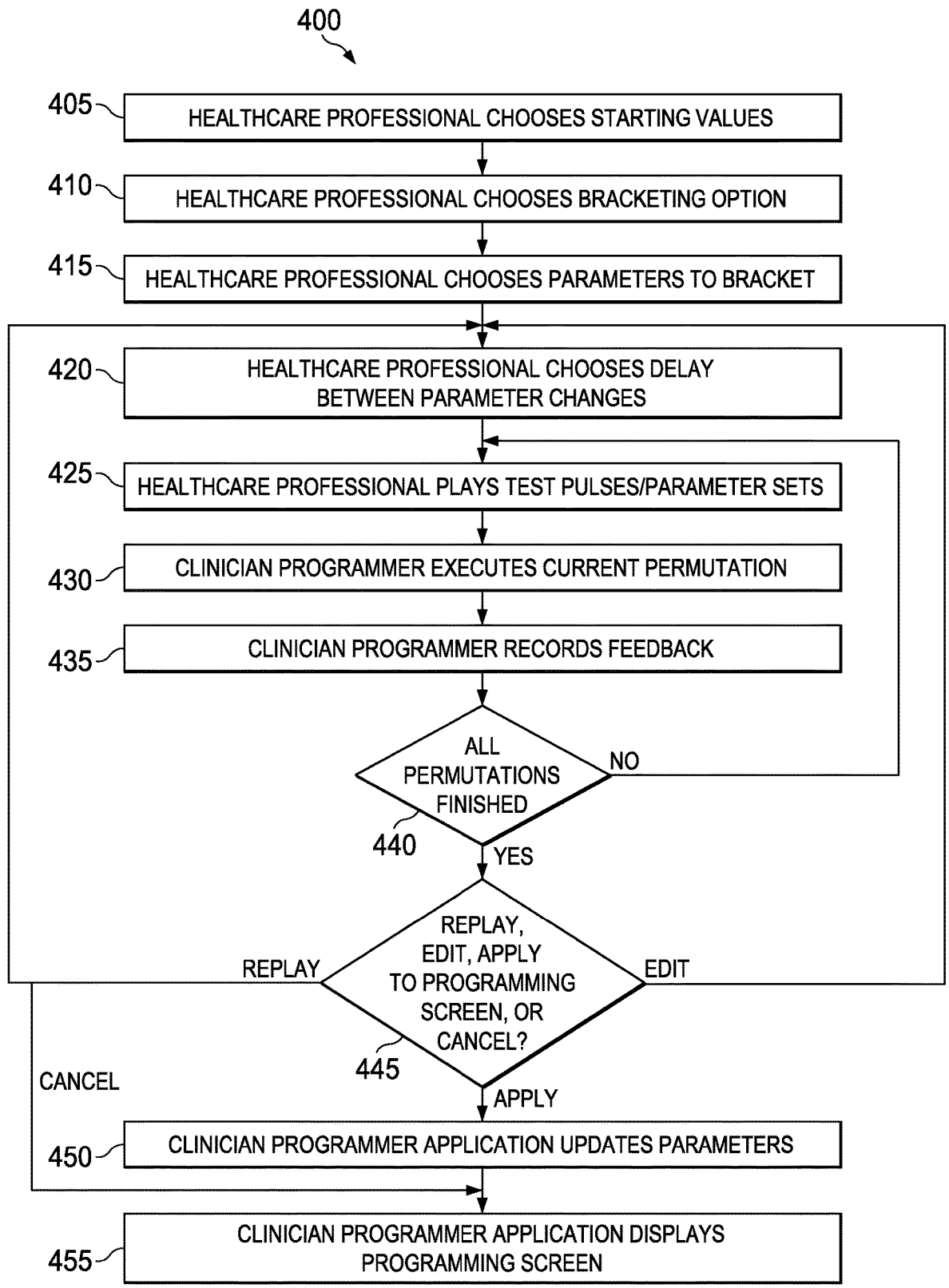

FIG. 10 is a simplified flowchart of a method 400 of programming stimulation parameters according to the various aspects of the present disclosure. The method 400 includes a step 405, in which the healthcare professional chooses the starting values for the stimulation parameters. The method 400 proceeds to a step 410, in which the healthcare professional chooses the bracketing option. The method 400 proceeds to a step 415, in which the healthcare professional chooses stimulation parameters to bracket. The method 400 proceeds to a step 420, in which the healthcare professional chooses the delay between the parameter changes. The method 400 proceeds to a step 425, in which the healthcare professional plays the test pulses/parameter sets. The method 400 proceeds to a step 430, in which the clinician programmer executes the current permutation. The method 400 proceeds to a step 435, in which the clinician programmer records the patient feedback. The method 400 proceeds to a decision step 440 to determine whether all permutations are finished. If the answer from the decision step 440 is no, then the method 400 loops back to the step 425. If the answer from the decision step 440 is yes, then the method 400 continues to a decision step 445 to determine which of the four options is chosen: "replay", "edit", "apply to programming screen", or "cancel". If the answer from the decision step 445 is "replay" or "edit", then the method 400 loops back to the step 420. If the answer from the decision step 445 is "apply", then the method 400 continues to a step 450, in which the clinician programmer application updates the stimulation parameters. The method 400 then continues with a step 455, in which the clinician programmer application displays the programming screen. If the answer from the decision step 445 is "cancel", then the method 400 proceeds to the step 455 directly.

Figure 11:
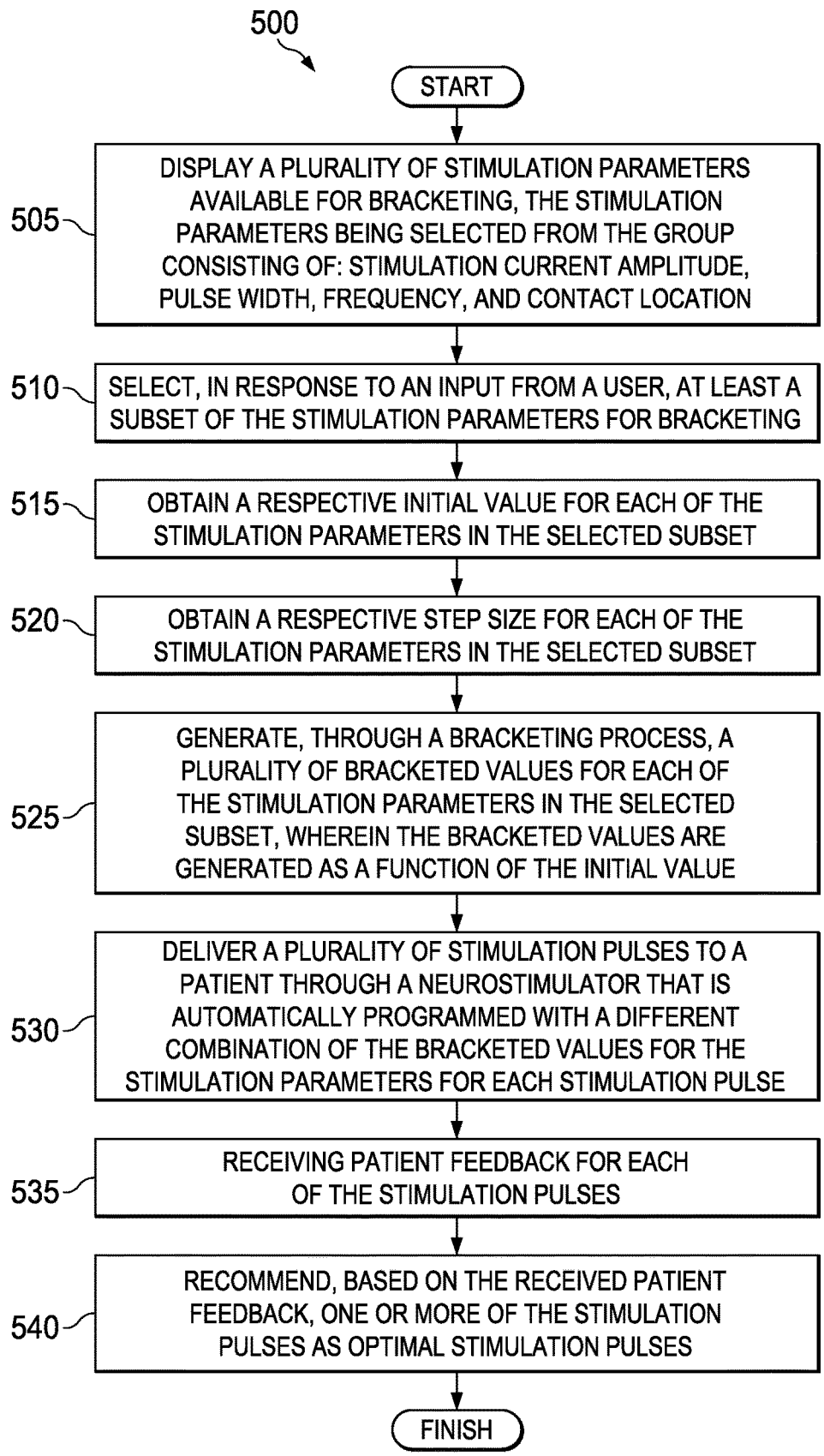

FIG. 11 is a simplified flowchart of a method 500 of setting stimulation parameters for neurostimulation according to various aspects of the present disclosure. The method 500 includes a step 505, in which a plurality of stimulation parameters available for bracketing are displayed. The stimulation parameters may include stimulation current amplitude, pulse width, frequency, or contact location.

The method 500 includes a step 510, in which at least a subset of the stimulation parameters is selected for bracketing selecting in response to an input from a user. In some embodiments, the selected subset contains at least two different types of stimulation parameters.

The method 500 includes a step 515, in which a respective initial value for each of the stimulation parameters in the selected subset is obtained. In some embodiments, the initial value is received from the user. In other embodiments, the initial value is calculated using a Computer Assisted Stimulation Programming (CASP) technique. The step 515 may be performed before or after the step 510.

The method 500 includes a step 520, in which a respective step size for each of the stimulation parameters in the selected subset is obtained.

The method 500 includes a step 525, in which a bracketing process is used to generate a plurality of bracketed values for each of the stimulation parameters in the selected subset. The bracketed values are generated as a function of the initial value. In some embodiments, the bracketed values for each stimulation parameter include the initial value. In some embodiments, the step 525 includes generating each bracketed value to be offset from the initial value by a different integer multiple of the step size associated with the stimulation parameter. In some embodiments, the initial value is a median of the bracketed values.

The method 500 includes a step 530, in which a plurality of stimulation pulses is delivered to a patient through a neurostimulator. The neurostimulator is automatically programmed (for example, without requiring user input) with a different combination of the bracketed values for the stimulation parameters for each stimulation pulse. In some embodiments, the step 530 is performed for a single contact having a first electrode polarity. In these embodiments, the step 530 may further include: assigning a second electrode polarity opposite the first electrode polarity to the single contact, and thereafter repeating the delivering for the single contact.

The method 500 includes a step 535, in which patient feedback is received for each of the stimulation pulses.

The method 500 includes a step 540, in which one or more of the stimulation pulses is recommended as optimal stimulation pulses based on the received patient feedback.

In some embodiments, one or more of the steps 505-540 may be performed by a clinician programmer having a touchscreen configured to display a touch-sensitive graphical user interface. In some embodiments, the touch-sensitive graphical user interface includes a programming screen for programming one or more contacts on an implanted lead. The programming screen contains a bracketing icon which, upon being pressed by the user, triggers the displaying of the plurality of stimulation parameters available for bracketing (i.e., step 505).

It is understood that additional process steps may be performed before, during, or after the steps 505-540. For example, the method 500 may include a step of selecting one or more electrodes for bracketing. For reasons of simplicity, other additional processes are not specifically discussed herein. Furthermore, the steps 505-540 need not be performed in the numerical order shown in FIG. 11. For example, the step 515 of "obtaining a respective initial value for each of the stimulation parameters" may be performed before the step 505 of "displaying a plurality of stimulation parameters available for bracketing."

Figure 12:
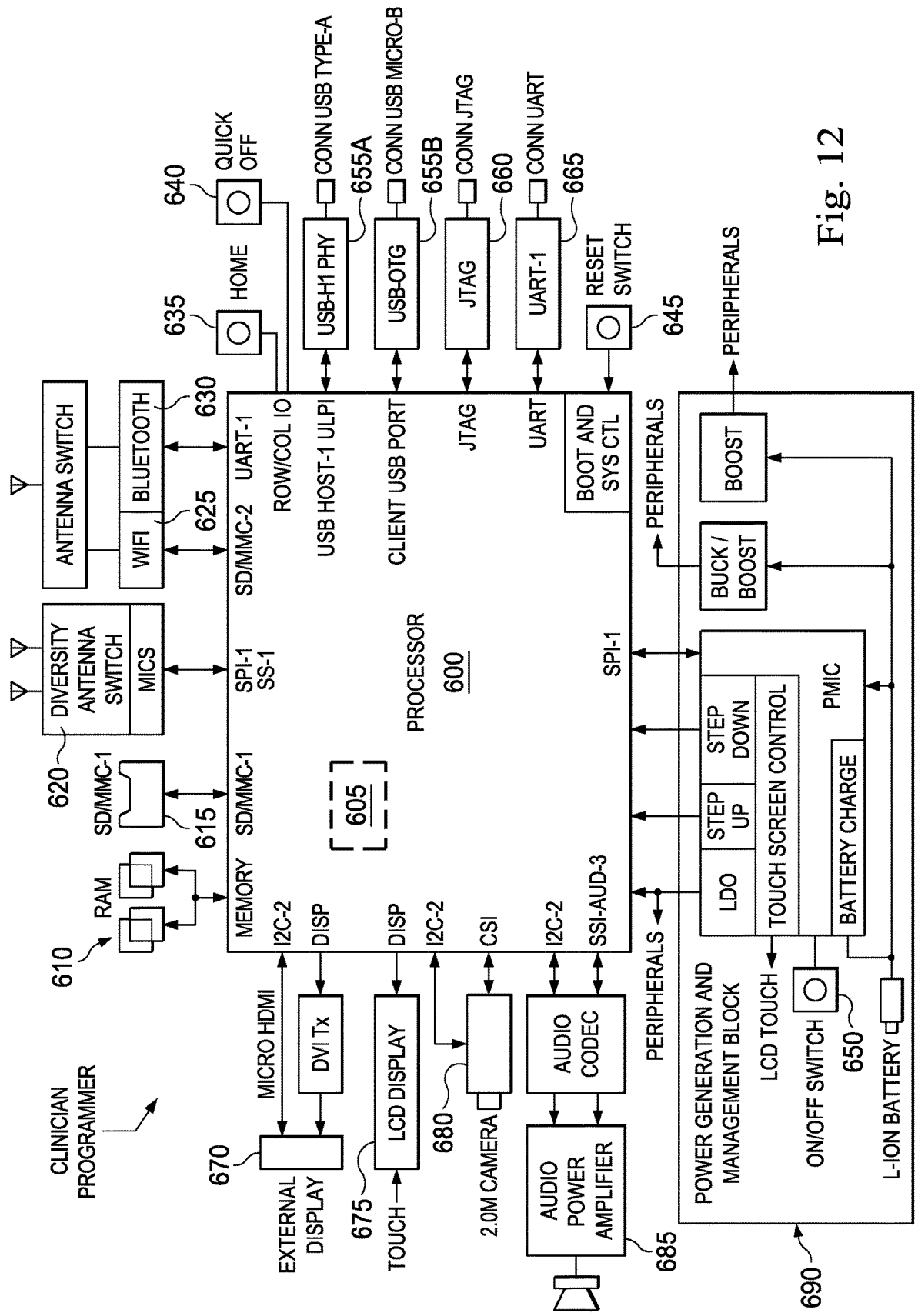
FIG. 12 is a simplified block diagram of an electronic programmer according to various aspects of the present disclosure.

FIG. 12 shows a block diagram of one embodiment of the electronic programmer (CP) discussed herein. For example, the electronic programmer may be a clinician programmer (CP) configured to perform the bracketing process discussed above. It is understood, however, that alternative embodiments of the electronic programmer may be used to perform these representations as well.

The CP includes a printed circuit board ("PCB") that is populated with a plurality of electrical and electronic components that provide power, operational control, and protection to the CP. With reference to FIG. 12, the CP includes a processor 600. The processor 600 controls the CP. In one construction, the processor 600 is an applications processor model i.MX515 available from FREESCALE Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX510EC, Rev. 4" data sheet dated August 2010 and published by FREESCALE Semiconductor® at WWW-.FREESCALE.COM. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 12 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 12.

The CP includes multiple bi-directional radio communication capabilities. Specific wireless portions included with the CP are a Medical Implant Communication Service (MICS) bi-directional radio communication portion 620, a Wi-Fi bi-directional radio communication portion 625, and a BLUETOOTH bi-directional radio communication portion 630. The MICS portion 620 includes a MICS communication interface, an antenna switch, and a related antenna, all of which allows wireless communication using the MICS specification. The Wi-Fi portion 625 and BLUETOOTH portion 630 include a Wi-Fi communication interface, a BLUETOOTH communication interface, an antenna switch, and a related antenna all of which allows wireless communication following the Wi-Fi Alliance standard and BLUETOOTH Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 12.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 12) may also be included for data transfer.

It is understood that a patient programmer may be implemented in a similar manner as the clinician programmer shown in FIG. 12.

Figure 13:
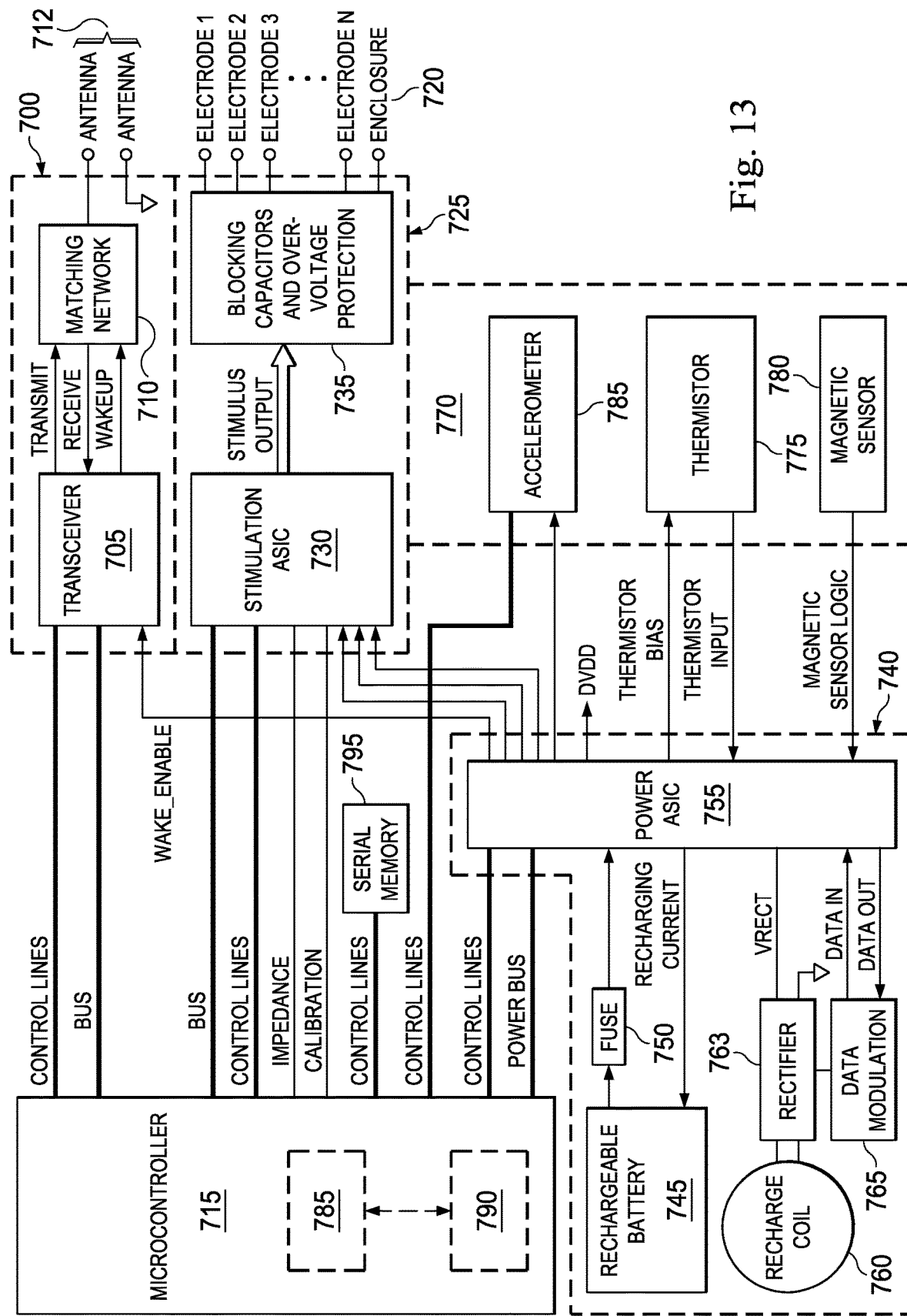
FIG. 13 is a simplified block diagram of an implantable medical device according to various aspects of the present disclosure.

FIG. 13 shows a block diagram of one embodiment of an implantable medical device. In the embodiment shown in FIG. 13, the implantable medical device includes an implantable pulse generator (IPG). The IPG includes a printed circuit board ("PCB") that is populated with a plurality of electrical and electronic components that provide power, operational control, and protection to the IPG. With reference to FIG. 13, the IPG includes a communication portion 700 having a transceiver 705, a matching network 710, and antenna 712. The communication portion 700 receives power from a power ASIC (discussed below), and communicates information to/from the microcontroller 715 and a device (e.g., the CP) external to the IPG. For example, the IPG can provide bi-direction radio communication capabilities, including Medical Implant Communication Service (MICS) bi-direction radio communication following the MICS specification.

The IPG provides stimuli to electrodes of an implanted medical electrical lead (not illustrated herein). As shown in FIG. 13, N electrodes are connected to the IPG. In addition, the enclosure or housing 720 of the IPG can act as an electrode. The stimuli are provided by a stimulation portion 225 in response to commands from the microcontroller 215. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, FLASH, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 13 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a signal from the CP.

Figure 14:
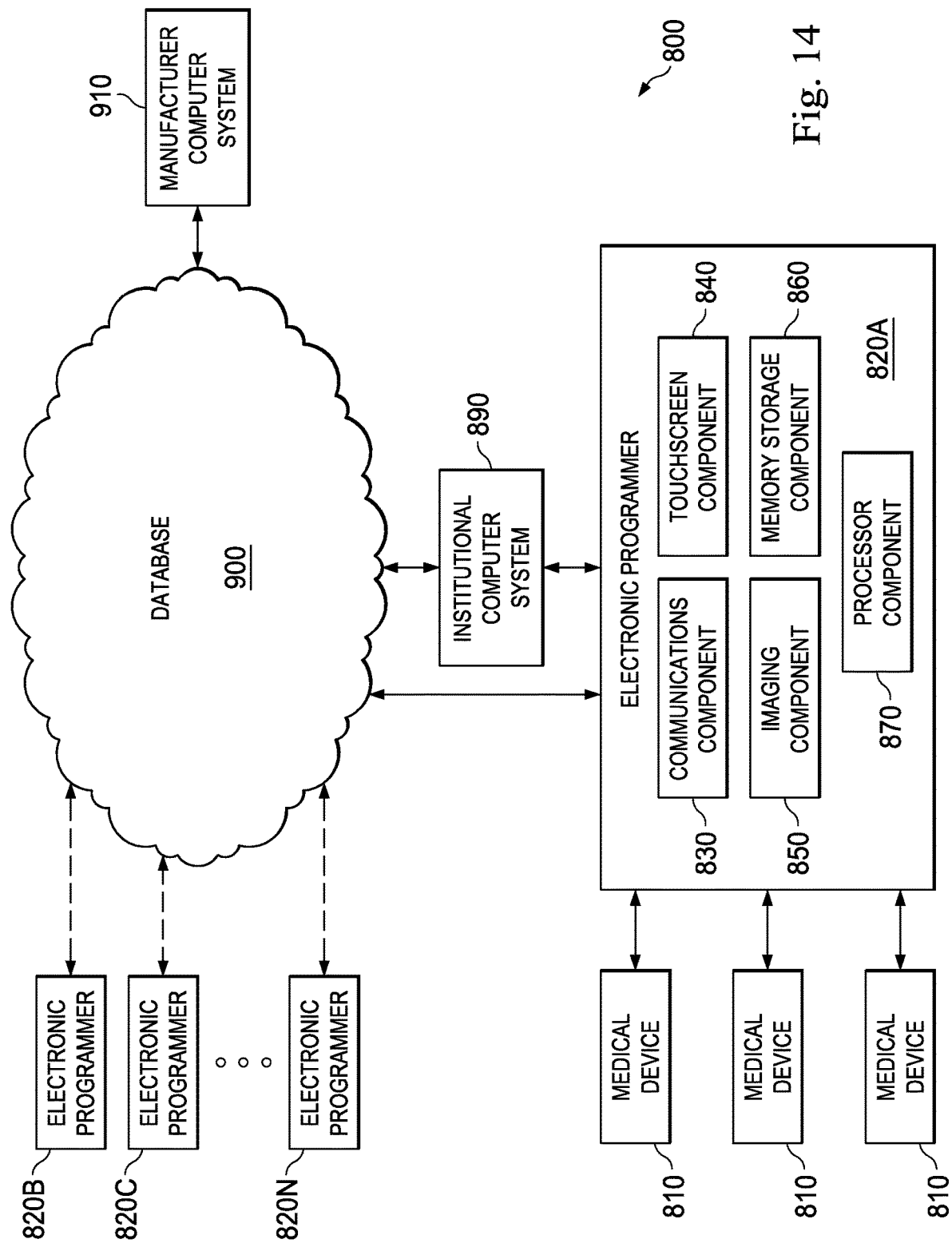
FIG. 14 is a simplified block diagram of a medical system/infrastructure according to various aspects of the present disclosure.

Referring now to FIG. 14, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above with reference to FIG. 1. For example, the medical devices 810 may be a pulse generator (e.g., the IPG discussed above with reference to FIG. 13), an implantable lead, a charger, or portions thereof. It is understood that each of the medical devices 810 may be a different type of medical device. In other words, the medical devices 810 need not be the same type of medical device.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIG. 12. In other embodiments, the electronic programmer 820A may be a patient programmer or another similar programmer. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (BLUETOOTH), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage 608 (e.g., ROM), or a disk drive (e.g., magnetic or optical), or any other suitable types of computer readable storage media.

For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 14 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, electronic data, such as pain and stimulation maps (collectively referred to as sensation maps) may be uploaded from the electronic programmer 820A to the database 900. The sensation maps are discussed in more detail in provisional U.S. Patent Application No. 61/695,407, filed on Aug. 31, 2012, entitled "Method and System of Producing 2D Representations of 3D Pain and Stimulation Maps and Implant Models on a Clinician Programmer," and provisional U.S. Patent Application No. 61/695,721, filed on Aug. 31, 2012, entitled "Method and System of Creating, Displaying, and Comparing Pain and Stimulation Maps," and provisional U.S. Patent Application No. 61/695,676, filed on Aug. 31, 2012, entitled "Method and System of Adjusting 3D Models of Patients on a Clinician Programmer," the disclosures of each of which are hereby incorporated by reference in their entirety.

The sensation maps saved in the database 900 may thereafter be downloaded by any of the other electronic programmers 820B-820N communicatively coupled to it, assuming the user of these programmers has the right login permissions. For example, after the 2D sensation map is generated by the electronic programmer 820A and uploaded to the database 900. That 2D sensation map can then be downloaded by the electronic programmer 820B, which can use the downloaded 2D sensation map to reconstruct or recreate a 3D sensation map. In this manner, a less data-intensive 2D sensation map may be derived from a data-heavy 3D sensation map, sent to a different programmer through the database, and then be used to reconstruct the 3D sensation map.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

Figure 15B:
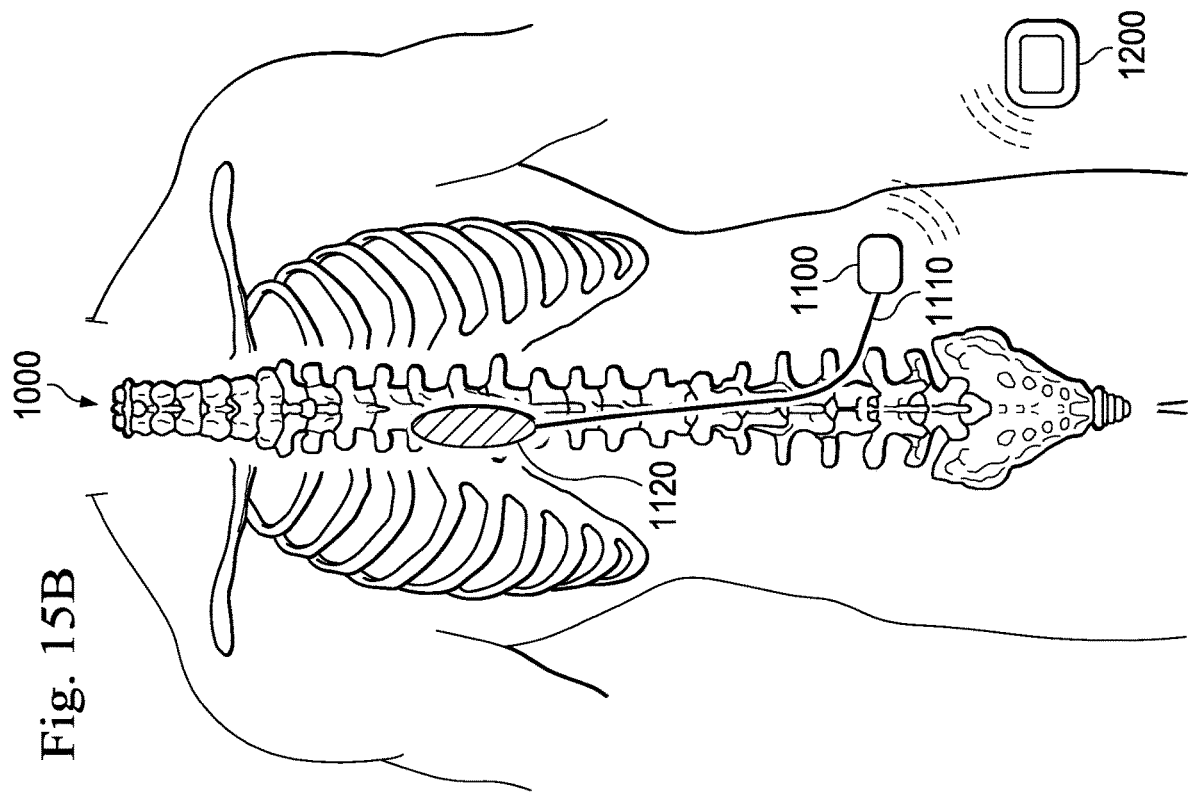
FIGS. 15A and 15B are side and posterior views of a human spine, respectively.
Figure 15A:
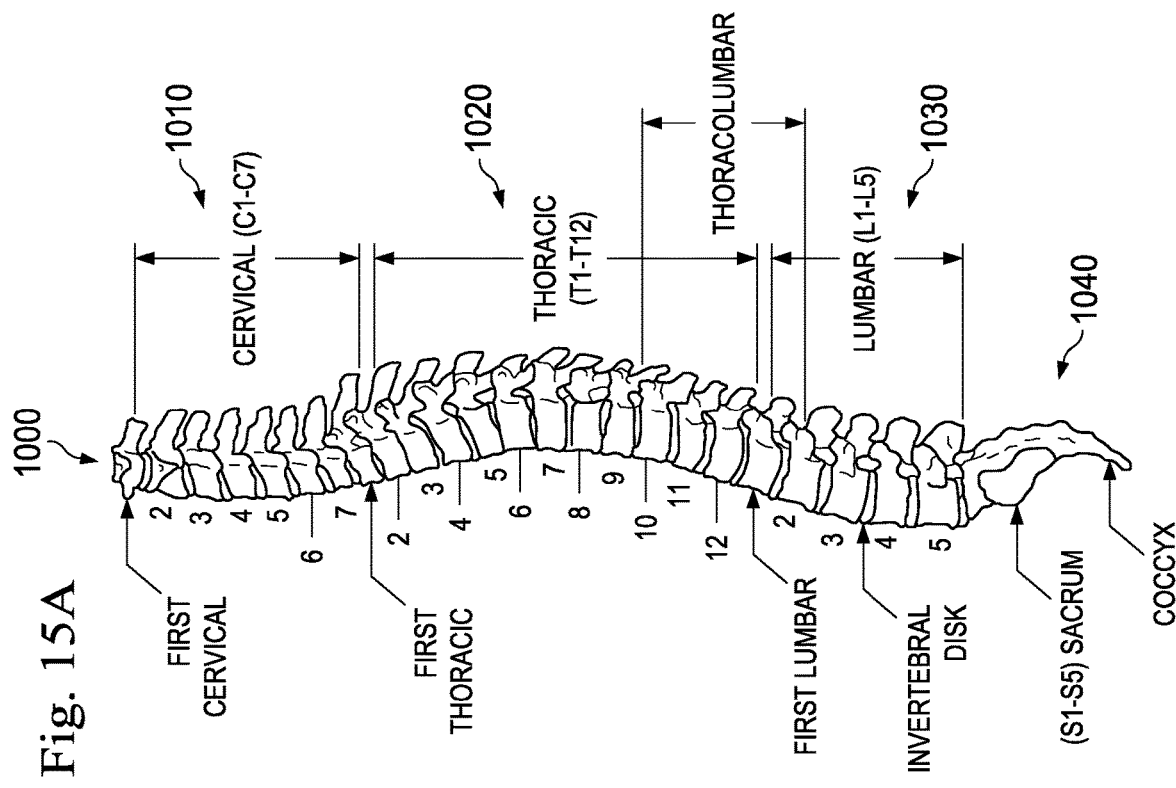

FIG. 15A is a side view of a spine 1000, and FIG. 15B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 15B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 12.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An electronic device for setting stimulation parameters of a neurostimulator to deliver neurostimulation to a patient, the electronic device comprising:
    a user interface;
    a memory storage component configured to store programming code; and
    a computer processor configured to execute the programming code to perform the following tasks:
        displaying a plurality of stimulation parameters available for bracketing, the stimulation parameters being selected from the group consisting of:
        stimulation current amplitude, pulse width, frequency, and contact location;
        selecting, in response to an input from a user, at least a subset of the stimulation parameters for bracketing;
        obtaining a respective initial value for each of the stimulation parameters in the selected subset;
        generating, through a bracketing process, a plurality of bracketed values for each of the stimulation parameters in the selected subset, wherein the bracketed values are generated as a function of the initial value, wherein a first subset of the bracketed values are each greater than the initial value, and wherein a second subset of the bracketed values are each less than the initial value;

receiving, via the user interface, a specified length of a pause between consecutive stimulation pulses; and automatically programming the neurostimulator to deliver a plurality of stimulation pulses to the patient, wherein a different combination of the bracketed values is programmed into the neurostimulator for each stimulation pulse, and wherein the automatically programming is performed without requiring user input and includes automatically pausing stimulation according to the specified length between consecutive ones of the stimulation pulses.

2. The electronic device of claim 1, wherein the tasks further comprise:

receiving patient feedback for each of the stimulation pulses; and recommending, based on the received patient feedback, one or more of the stimulation pulses as optimal stimulation pulses.

3. The electronic device of claim 1, wherein the selected subset contains at least two different types of stimulation parameters, and wherein at least one of the stimulation parameters is a stimulation frequency or a stimulation pulse width.

4. The electronic device of claim 1, wherein the bracketed values for each stimulation parameter include the initial value.

5. The electronic device of claim 1, wherein the tasks further comprise: obtaining a respective step size for each of the stimulation parameters in the selected subset.

6. The electronic device of claim 5, wherein the generating the bracketed values comprises generating each bracketed value to be offset from the initial value by a different integer multiple of the step size associated with the stimulation parameter, and wherein the initial value is a median of the bracketed values.

7. The electronic device of claim 1, wherein the automatically programming is performed for a single contact having a first electrode polarity, and wherein the tasks further comprise:

assigning a second electrode polarity opposite the first electrode polarity to the single contact; and thereafter repeating the automatically programming for the single contact.

8. The electronic device of claim 1, wherein the obtaining the respective initial value comprises receiving the respective initial value from the user or calculating the initial values using a Computer Assisted Stimulation Programming (CASP) technique.

9. The electronic device of claim 1, wherein the user interface comprises a touchscreen.

10. The electronic device of claim 9, wherein the user interface is configured to display a programming screen for programming one or more electrodes on an implanted lead, the programming screen containing a bracketing icon which, upon being pressed by the user, triggers the displaying of the plurality of stimulation parameters available for bracketing.

11. A medical system, comprising:

a neurostimulator configured to deliver electrical stimulation to a patient via one or more of a plurality of contacts located on a lead; and a portable electronic programmer having an electronic processor and a touch-sensitive graphical user interface, wherein the electronic programmer is configured to:

display, through the touch-sensitive graphical user interface, a plurality of stimulation parameters available for bracketing, the stimulation parameters being selected from the group consisting of: stimulation current amplitude, pulse width, frequency, and contact location;

select, in response to a user input received through the touch-sensitive graphical user interface, at least a subset of the stimulation parameters for bracketing;

obtain a respective initial value for each of the stimulation parameters in the selected subset;

generate, through a bracketing process performed by the electronic processor, a plurality of bracketed values for each of the stimulation parameters in the selected subset, wherein the bracketed values are generated as a function of the initial value, wherein at least some of the bracketed values are each greater than the initial value;

receiving, via the touch-sensitive graphical user interface, a specified length of a pause between consecutive stimulation pulses; and automatically program, without requiring any user input, the neurostimulator to deliver a plurality of stimulation pulses to the patient, wherein a different combination of the bracketed values is programmed into the neurostimulator for each stimulation pulse, and wherein the neurostimulator is automatically programmed without requiring user input, and wherein the stimulation pulses are automatically paused according to the specified length between consecutive ones of the stimulation pulses.

12. The medical system of claim 11, further comprising a patient feedback tool, and wherein the electronic programmer is further configured to:

receive, through the patient feedback tool, patient feedback for each of the stimulation pulses; and recommend, based on the received patient feedback, one or more of the stimulation pulses as optimal stimulation pulses.

13. The medical system of claim 11, wherein the selected subset contains at least two different types of stimulation parameters, and wherein at least one of the stimulation parameters is a stimulation frequency or a stimulation pulse width.

14. The medical system of claim 11, wherein the bracketed values for each stimulation parameter include the initial value.

15. The medical system of claim 11, wherein the electronic programmer is further configured to: obtain a respective step size for each of the stimulation parameters in the selected subset.

16. The medical system of claim 15, wherein each bracketed value is offset from the initial value by a different integer multiple of the step size associated with the stimulation parameter, and wherein the initial value is a median of the bracketed values.

17. The medical system of claim 11, wherein the electronic programmer is configured to program a single contact of the neurostimulator having a first electrode polarity, and wherein the electronic programmer is further configured to:

assign a second electrode polarity opposite the first electrode polarity to the single contact; and thereafter repeat a programming of the neurostimulator to deliver the plurality of stimulation pulses for the single contact.

18. The medical system of claim 11, wherein the respective initial values are received from the user or calculated using a Computer Assisted Stimulation Programming (CASP) technique.

19. The medical system of claim 11, wherein the electronic programmer has a touchscreen configured to display the touch-sensitive graphical user interface, and wherein the touch-sensitive graphical user interface includes a programming screen for programming one or more contacts on the lead, the programming screen containing a bracketing icon which, upon being pressed by the user, triggers the display of the plurality of stimulation parameters available for bracketing.

20. An electronic apparatus for setting stimulation parameters of a neurostimulator to deliver neurostimulation, the electronic apparatus comprising:
input/output means for communicating with a user, the input/output means including a touch-sensitive screen configured to detect an input from the user and display an output to the user;
memory storage means for storing executable instructions; and
computer processor means for executing the instructions to perform the following tasks:
displaying a plurality of stimulation parameters available for bracketing, the stimulation parameters being selected from the group consisting of: stimulation current amplitude, pulse width, frequency, and contact location;
selecting, in response to an input from a user, at least a subset of the stimulation parameters for bracketing;
obtaining a respective initial value for each of the stimulation parameters in the selected subset;
generating, through a bracketing process, a plurality of bracketed values for each of the stimulation parameters in the selected subset, wherein the bracketed values are generated as a function of the initial value, wherein the bracketed values include values that are greater than the initial value and values that are less than the initial value;
receiving, via the input/output means, a specified length of a pause between consecutive stimulation pulses; and
automatically programming, without requiring user input, the neurostimulator to deliver a plurality of stimulation pulses to a patient, wherein a different combination of the bracketed values is programmed into the neurostimulator for each stimulation pulse, and wherein the automatically programming is performed without requiring user input and includes automatically pausing stimulation according to the specified length between consecutive ones of the stimulation pulses.

21. The electronic apparatus of claim 20, wherein the tasks further comprise:
receiving patient feedback for each of the stimulation pulses; and
recommending, based on the received patient feedback, one or more of the stimulation pulses as optimal stimulation pulses.

22. The electronic apparatus of claim 20, wherein the selected subset contains at least two different types of stimulation parameters, and wherein at least one of the stimulation parameters is a stimulation frequency or a stimulation pulse width.

23. The electronic apparatus of claim 20, wherein the bracketed values for each stimulation parameter include the initial value.

24. The electronic apparatus of claim 20, wherein the tasks further comprise: obtaining a respective step size for each of the stimulation parameters in the selected subset.

25. The electronic apparatus of claim 24, wherein the generating the bracketed values comprises generating each bracketed value to be offset from the initial value by a different integer multiple of the step size associated with the stimulation parameter, and wherein the initial value is a median of the bracketed values.

26. The electronic apparatus of claim 20, wherein the automatically programming is performed for a single contact having a first electrode polarity, and wherein the tasks further comprise:
assigning a second electrode polarity opposite the first electrode polarity to the single contact; and
thereafter repeating the automatically programming for the single contact.

27. The electronic apparatus of claim 20, wherein the obtaining the respective initial value comprises receiving the respective initial value from the user or calculating the initial values using a Computer Assisted Stimulation Programming (CASP) technique.

28. The electronic apparatus of claim 20, wherein the touch-sensitive screen is configured to display a programming screen for programming one or more electrodes on an implanted lead, the programming screen containing a bracketing icon which, upon being pressed by the user, triggers the displaying of the plurality of stimulation parameters available for bracketing.

29. An electronic device for setting stimulation parameters of a neurostimulator to deliver neurostimulation to a patient, the electronic device comprising:
a graphical user interface configured to receive an input from, and display an output to, a user;
a memory storage component configured to store programming code; and
a computer processor configured to execute the programming code to perform operations comprising:
displaying, via the graphical user interface, a plurality of stimulation parameters eligible for bracketing, the stimulation parameters being selected from the group consisting of: stimulation current amplitude, pulse width, frequency, and contact location;
selecting at least a subset of the stimulation parameters for bracketing;
obtaining a respective initial value for each of the stimulation parameters in the selected subset;
receiving, via the graphical user interface, a specified length of a pause between consecutive stimulation pulses of a plurality of stimulation pulses;
generating, through a bracketing process, a plurality of bracketed values for each of the stimulation parameters in the selected subset, wherein the bracketed values are generated based on the initial value, wherein a first subset of the bracketed values are each greater than the initial value, and wherein a second subset of the bracketed values are each less than the initial value; and
causing a pulse generator to deliver a plurality of stimulation pulses to a patient by automatically programming the pulse generator with a different combination of the bracketed values for the stimulation parameters for each stimulation pulse, and wherein the automatically programming is performed without requiring user input and includes automatically pausing stimulation according to the specified length between consecutive ones of the stimulation pulses.

30. The electronic device of claim 29, wherein the first subset of the bracketed values and the second subset of the bracketed values are symmetrically distributed with respect to the initial value.

31. The electronic device of claim 30, wherein the pulse generator is programmed to deliver the stimulation pulses for a single contact having a first electrode polarity, and wherein the operations further comprise:
  assigning a second electrode polarity opposite the first electrode polarity to the single contact; and
  thereafter causing the pulse generator to deliver the stimulation pulses again for the single contact.

32. The electronic device of claim 29, wherein the operations further comprise:
  receiving patient feedback for each of the stimulation pulses; and
  recommending, based on the received patient feedback, one or more of the stimulation pulses as optimal stimulation pulses.

33. The electronic device of claim 29, wherein the selected subset contains at least two different types of stimulation parameters, and wherein at least one of the stimulation parameters is a stimulation frequency or a stimulation pulse width.

34. The electronic device of claim 29, wherein the bracketed values for each stimulation parameter include the initial value.

35. The electronic device of claim 29, wherein the operations further comprise: obtaining a respective step size for each of the stimulation parameters in the selected subset.

36. The electronic device of claim 35, wherein the generating the bracketed values comprises generating each bracketed value to be offset from the initial value by a different integer multiple of the step size associated with the stimulation parameter, and wherein the initial value is a median of the bracketed values.

37. The electronic device of claim 29, wherein the obtaining the respective initial value comprises receiving the respective initial value from the user or calculating the initial values using a Computer Assisted Stimulation Programming (CASP) technique.

38. The electronic device of claim 29, wherein the operations further comprise displaying a programming screen for programming one or more contacts on an implanted lead, the programming screen containing a bracketing icon which, upon being engaged by the user, triggers the displaying of the plurality of stimulation parameters eligible for bracketing.

* * * * *